United States Patent [19]

Knauer

[11] Patent Number: 5,514,097

[45] Date of Patent: May 7, 1996

[54] SELF ADMINISTERED INJECTION PEN APPARATUS AND METHOD

[75] Inventor: Peter M. Knauer, San Carlos, Calif.

[73] Assignee: Genentech, Inc., South San Francisco, Calif.

[21] Appl. No.: 195,307

[22] Filed: Feb. 14, 1994

[51] Int. Cl.⁶ .................................................... A61M 5/20
[52] U.S. Cl. ......................... 604/136; 604/187; 604/198; 604/218
[58] Field of Search ........................... 604/131, 135–139, 604/156, 187, 208, 211, 218, 220, 232

[56] References Cited

U.S. PATENT DOCUMENTS

| | | |
|---|---|---|
| 3,905,365 | 9/1975 | Colombo . |
| 4,394,863 | 7/1983 | Bartner . |
| 4,405,317 | 9/1983 | Case . |
| 4,413,760 | 11/1983 | Paton . |
| 4,498,904 | 2/1985 | Turner et al. . |
| 4,585,439 | 4/1986 | Michel . |
| 4,601,708 | 7/1986 | Jordan . |
| 4,642,099 | 2/1987 | Phillips et al. . |
| 4,673,396 | 6/1987 | Urbaniak . |
| 4,701,165 | 10/1987 | DeHaitre . |
| 4,755,169 | 7/1988 | Sarnoff et al. . |
| 4,832,690 | 5/1989 | Kuu . |
| 4,865,591 | 9/1989 | Sams . |
| 4,874,383 | 10/1989 | McNaughton . |
| 4,883,472 | 11/1989 | Michel . |
| 4,931,043 | 6/1990 | Ray et al. . |
| 4,936,833 | 6/1990 | Sams . |
| 4,966,585 | 10/1990 | Gangemi . |
| 4,968,299 | 11/1990 | Ahlstrand et al. . |
| 4,969,874 | 11/1990 | Michel et al. . |
| 5,017,190 | 5/1991 | Simon et al. . |
| 5,019,053 | 5/1991 | Hoffman et al. . |
| 5,032,114 | 7/1991 | Olovson . |
| 5,042,977 | 8/1991 | Bechtold et al. . |
| 5,050,617 | 9/1991 | Columbus et al. . |
| 5,085,641 | 2/1992 | Sarnoff et al. . |
| 5,085,642 | 2/1992 | Sarnoff et al. . |
| 5,092,842 | 3/1992 | Bechtold et al. . |
| 5,104,380 | 4/1992 | Holman et al. . |
| 5,112,317 | 5/1992 | Michel . |
| 5,114,406 | 5/1992 | Gabriel et al. . |
| 5,176,657 | 1/1993 | Shields . |
| 5,226,895 | 7/1993 | Harris . |
| 5,226,896 | 7/1993 | Harris . |
| 5,232,459 | 8/1993 | Hjertman . |
| 5,244,465 | 9/1993 | Michel . |
| 5,273,544 | 12/1993 | van der Wal . |

FOREIGN PATENT DOCUMENTS

| | | |
|---|---|---|
| 0268191A2 | 11/1987 | European Pat. Off. . |
| 0327910A2 | 8/1989 | European Pat. Off. . |
| 0373321A1 | 10/1989 | European Pat. Off. . |
| 0496141 | 7/1992 | European Pat. Off. . |
| 0525525 | 2/1993 | European Pat. Off. . |
| 0557559A1 | 9/1993 | European Pat. Off. . |
| 8813905 | 12/1989 | Germany . |
| WO87/02895 | 5/1987 | WIPO . |
| WO90/04423 | 5/1990 | WIPO . |
| 9310838 | 6/1993 | WIPO . |
| WO93/16740 | 9/1993 | WIPO . |

Primary Examiner—C. Fred Rosenbaum
Assistant Examiner—Perry E. Van Over
Attorney, Agent, or Firm—Skjerven, Morrill, MacPherson, Franklin & Friel; Forrest E. Gunnison; Philip J. McKay

[57] ABSTRACT

A medicament injection apparatus for subcutaneous or intramuscular delivery of a medicament conceals the needle behind a needle shroud. On apparatus activation, the needle is trust forward, pushing the needle tip outside the needle shroud with enough force to puncture the skin. The needle is thus automatically introduced into the tissue at the proper needle\skin orientation. In the same action, the apparatus automatically dispenses an accurate pre-set dose. The dose can be set by a manual, variable dosing assembly or by an automatic dosing assembly. The automatic dosing assembly includes a safety mechanism preventing the pre-set dose from being changed except by a doctor or patient using a special wrench or tool.

62 Claims, 16 Drawing Sheets

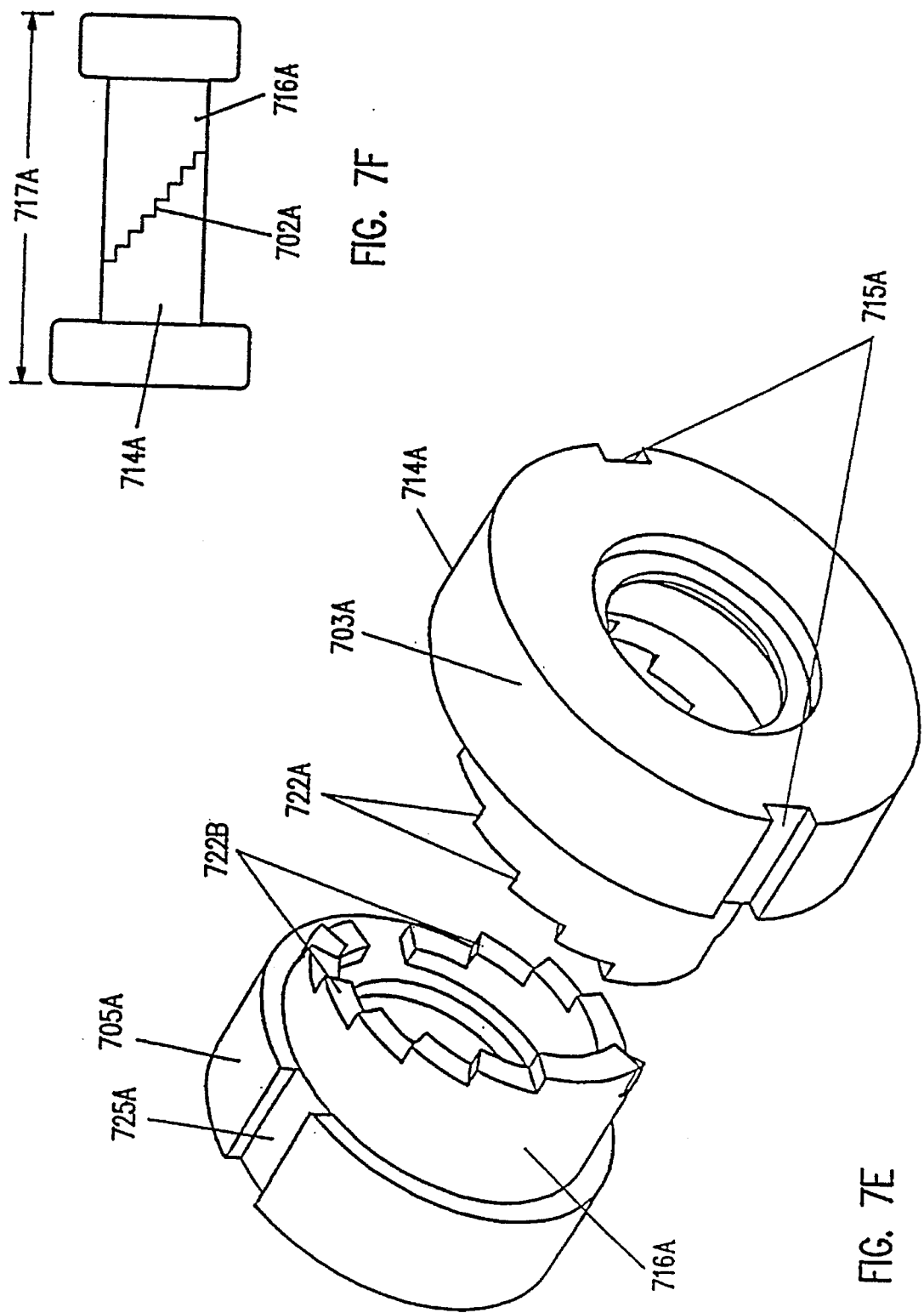

SELF ADMINISTERED INJECTION PEN APPARATUS AND METHOD

FIELD OF THE INVENTION

This invention relates, generally, to medicament delivery apparatuses, and, more particularly, to self administered injection pen apparatuses.

BACKGROUND OF THE INVENTION

Self administered subcutaneous or intramuscular injections are well known in the medical arts and have long been considered standard treatment for those persons, such as diabetics, who require fixed or measured doses of medicament on a regular and relatively frequent basis. Further, newer treatments, such as growth hormone injections, also require self administered injections on a regular basis.

Self administered injections considerably decrease the cost of treatment and increase the quality of the patients life by decreasing or even eliminating the need for some visits to the doctor. Self administered injections also provide patients with the opportunity to privately administer their own treatment, without involving third parties, thus giving the patient a sense of independence and control.

Typically, self administered injections were rendered using common syringes adapted to receive cartridges of pre-measured doses of medicament. However, such self administered injections suffered from several drawbacks and were particularly ill suited for use by children or patients with disabilities because they required the patient to manually insert an exposed needle in the tissue.

FIG. 1 is a cross-sectional view of a typical prior art injection pen 11. Injection pen 11 had three major components: (i) a pre-filled medicament cartridge assembly 10 containing a medicament 28; (ii) a cartridge housing 16 formed to receive pre-filled medicament cartridge assembly 10, and having a double sided needle assembly 13 mounted on one end 20; and (iii) a dispensing assembly 21. Each of the three major components are described more completely below. For a more complete description of a particular injection pen 11, see commonly assigned U.S. patent application Ser. No. 08/146,313 entitled "An Injection Pen Solution Transfer Apparatus and Method" of Peter Michel, Robert Freeman, James Oeswein filed on Nov. 2, 1993, which is incorporated herein by reference in its entirety.

End 12 of pre-filled medicament cartridge assembly 10 has a seal assembly 26 that is pierced and penetrated by needle 27 to dispense medicament 28. A second end 14 of pre-filled medicament cartridge assembly 10, that is opposite to end 12, is sealed by a slidable plunger 15.

Typically, cartridge housing 16 receives the pre-filled medicament cartridge assembly 10 through an open end 17. End 20 of cartridge housing 16, that is opposite open end 17, is generally removably mounted to double sided needle assembly 13 for subcutaneous or intramuscular injection of medicament 28. Removably mounted to end 17 is a dispensing assembly 21 that is operably coupled to cartridge plunger 15.

Specifically, a cartridge seat 22 of dispensing assembly 21 is formed to mount directly to sleeve 16, via mating threads 23. Upon mounting dispensing assembly 21 to cartridge housing 16, end 12 of medicament cartridge assembly 10 is forced into engagement with needle assembly 13. A pushrod 24, having a pushrod piston head 18, which abuts a backside 25 of plunger 15, is mounted to cartridge seat 22 to permit axial movement in a direction toward needle assembly 13. The movement of plunger 15 towards end 12 controls the volume of medicament expelled through needle assembly 13.

Prior art injection pen device 11 has no mechanism for allowing the introduction of an accurate dose less than the entire content of medicament cartridge assembly 10. Several improvements have been made on this basic design which deliver portions of medicament 28 in medicament cartridge assembly 10 in pre-set doses. However, the improved versions require considerable patient interaction with some form of relatively complicated dosing mechanism to set the dose with each injection.

Typically, prior art medicament injection devices require the patient to manually insert an exposed needle into his or her own tissue. For many patients this is a traumatic routine. Often injections are necessary on a daily basis which can result in considerable psychological damage to the patient and his or her attitude towards treatment. In many cases the patient simply stops giving himself or herself treatment; adopting the attitude that the cure is worse than the affliction. Patient non-compliance is a particularly poignant problem when the patient is a child and, unfortunately, children make up a considerable percentage of those patients taking part in treatment programs requiring self administered subcutaneous or intramuscular injections. For instance, at present, in the United States, growth hormone treatment is only approved for children. Additionally, many diabetics must begin insulin treatment at an early age.

Further, when a patient manually inserts a needle there is a strong possibility that the patient will not place the needle in the proper orientation relative to the skin. The needle typically should enter the body perpendicular to the skin surface. If the patient is traumatized by the treatment routine, or is under time pressure, a sloppy and ineffective injection is likely to result from a non-perpendicular injection. When the needle enters the tissue at the wrong needle/skin orientation the injection may fail to properly introduce the medicament. Such improperly oriented injections, of course, are, at best, a waste of costly medicament and, at worst, may be dangerous.

Yet another difficulty with prior art injection pens is that the dose-setting mechanisms are complicated and usually involve reading some form of digital or analog meter while setting the dose. These prior art injection pens do not allow the patient to accurately set the dose in the event that the patient is either disabled or in a state incapable of reading a dose meter or setting some relatively complicated analog device.

Prior art dose-setting mechanisms using dose meter displays alone are a particular problem for diabetics who, because of their disease, are often blind. However, any patient who is either permanently or temporarily disabled, or is in an emergency situation, may find prior art dose mechanisms inadequate or perhaps useless.

Another problem is that two different unit systems for measuring the dose are commonly used; milliliters (ml) and international units (IU). In some cases, the patient can become confused as to which units the prior art dose meter is displaying. This situation can lead to improper dosage which, of course, is dangerous. Thus, while prior art injection pens are better than a syringe, such injection pens are not suitable for use in a wide variety of circumstances.

SUMMARY OF THE INVENTION

According to the principles of this invention, a medicament injection apparatus automatically administers a predetermined dose of a medicament, sometimes called a pre-set dose, for either a subcutaneous or intramuscular injection when the patient activates a dose knob of the medicament injection apparatus. When activated, the medicament injection apparatus of this invention pushes a plurality of assemblies that include a needle, in one embodiment, forward with sufficient force that the needle penetrates the patient's skin and then the medicament injection apparatus dispenses a predetermined and pre-set dose of medicament into the patient's tissue. The patient is thereby spared the trauma of manually introducing an exposed needle into his or her own tissue. Further, the medicament injection apparatus of this invention includes an automatic dosing assembly which requires minimal patient manipulation to automatically set the predetermined dose. This feature allows the medicament injection apparatus to be used safely by disabled patients and patients in emergency situations.

In one embodiment, the medicament injection apparatus of this invention includes a housing which encloses an interior volume. The housing has a first end and an second end opposite the first end. One end of a needle shroud is removably affixed to the first end of the housing. An opposite end of the needle shroud, removed from the housing, is open.

A medicament injection assembly, that includes a plurality of assemblies including, for example, a medicament cartridge assembly and a variable dosing assembly, is movably mounted within the housing so that upon engagement and activation of a motive force that is supplied by the medicament injection assembly, the plurality of assemblies move from a first position to a second position. This motion, which is supplied by a thrusting assembly, moves not only the entire plurality of assemblies but also subassemblies and parts within those plurality of assemblies to deliver the desired dose of medicament. In contrast, typically in prior systems, the only movement was of the parts required to deliver a dose and movement of entire assemblies was not provided because the user manually injected the needle into the skin.

The medicament injection assembly can include a needle attached at an end closest to the needle shroud open end. In one embodiment, the needle is protected with a needle safety cap that encloses the needle.

The plurality of assemblies are removably affixed to one another by threads or some other mechanism which allows the assemblies to be connected and disconnected from each other. For example, the medicament cartridge assembly is configured to contain a vial of medicament. When the medicament cartridge assembly is removably affixed to the variable dosing assembly, the vial is positioned within the medicament cartridge assembly by a cartridge seat which is part of a pushrod subassembly which, in turn, is part of the variable dosing assembly. Specifically, the cartridge seat has threads on an exterior surface that interface with threads on an interior surface of the medicament cartridge assembly.

When the motive force of the medicament injection assembly moves the plurality of assemblies forward from the first position to the second position within the housing, one end of the needle extends a predetermined distance outside the open end of the needle shroud. The needle is thrust forward with sufficient force to penetrate the skin and extend into the tissue. The distance the needle extends outside the needle shroud can be adjusted by exchanging needle shrouds.

In one embodiment, the needle shroud is removably affixed to the housing by a simple friction mounting. Thus, in this embodiment, the needle shroud can be simply pulled off and another shroud attached in its place. This feature allows the same medicament injection apparatus to be used for different types of injections, i.e., intramuscular versus subcutaneous, and allows a single medicament injection apparatus to adapt to a growing child.

The needle shroud conceals the injection needle from the patient until the medicament injection assembly is activated. Thus, the patient is spared the trauma of handling an exposed needle prior to and during injection and, in contrast to prior art systems, the patient is not forced to manually introduce the needle into his or her own tissue or even see an exposed needle prior to and during injection.

Further, once the needle has been extended, the medicament injection assembly dispenses a predetermined and pre-set amount of medicament into the tissue. The amount of medicament dispensed can be manually pre-set or, in one embodiment, an automatic dose can be selected by a simple manipulation of a dose knob. This novel feature allows the patient to administer an accurate pre-set dose without having to read a dose meter or make complicated adjustments as was required by prior art dosing mechanisms. Thus, the medicament injection apparatus of this invention is ideal for disabled persons such as the blind and for use in emergency situations where time is critical.

Additionally, in one embodiment, the maximum automatic dose can be set by a doctor or patient with a special tool. Once the automatic dose is set it cannot be changed without this tool. The automatic dose is a pre-set maximum dose and therefore provides protection from accidental overdose. Even when the dose is set manually it cannot exceed the automatic dose.

Due to the simplicity of its operation and its safety features, the medicament injection apparatus of this invention is well suited for use by a wide range of patients including children and those with permanent or temporary disabilities. To use one embodiment of the medicament injection apparatus of this invention, the patient simply (i) energizes the motive force subassembly by cocking the medicament injection apparatus, (ii) removes the needle safety cap, (iii) turns the dose knob as far as it will turn in one direction, (iv) places the open end of the needle shroud over the injection site, and (v) depresses the dose knob. The result of these five simple steps is that the needle automatically enters the skin at the proper, substantially perpendicular, orientation and an accurate pre-set dose is delivered without the patient ever having seen the needle. Thus, the medicament injection apparatus of this invention is simpler to use and safer than prior art systems.

In one embodiment, the medicament injection assembly includes, in addition to the plurality of assemblies, an automatic dosing assembly mounted in the interior volume of the housing. Upon engagement and actuation of the medicament injection assembly, the automatic dosing assembly applies the motive force to the plurality of assemblies thereby moving the plurality of assemblies from the first position to the second position.

The automatic dosing assembly includes a thrusting assembly, and a dose knob stop assembly. The thrusting assembly includes a motive force subassembly that is selectively engaged and actuated by a user. Upon engagement and actuation of the motive force subassembly, the thrusting assembly moves the plurality of assemblies of the medicament injection assembly from the first position to the second position.

The thrusting assembly also includes a tubular dose knob that is selectively engaged with the variable dosing assembly of the medicament injection assembly. The tubular dose knob has a first open end and a second end opposite to the first open end. Upon engagement of the tubular dose knob with the variable dosing assembly and movement of the tubular dose knob in a selected direction, the user adjusts the amount of medicament dispensed from the medicament injection apparatus. Those skilled in the art will appreciate that the dose knob can be utilized independently of the other parts and assemblies in the automatic dosing assembly and that the tubular nature of the dose knob is illustrative of only one embodiment of the dose knob and is not intended to limit the invention to only the tubular configuration.

The dose knob stop subassembly is coupled to the tubular dose knob so that the dose knob stop assembly limits movement of the tubular dose knob in the selected direction which in turn limits the amount of the medicament to be dispensed from the medicament injection apparatus to a predetermined and pre-set limit. The dose knob stop assembly includes two structures that are coupled to the tubular dose knob. Each of the two structures has a surface. The two structures can be, for example, either angled cylinders or stepped angled cylinders.

The two structures are mounted so that the surfaces interact and interface with one another such that a combined length of the two structures is variable depending on a relative position of the two surfaces. The variable combined length determines the predetermined and pre-set limit.

A dose-limiting sleeve is coupled to at least one of the two structures. The dose limiting sleeve can be selectively engaged by the user, e.g., engaged by the user via use of a special tool, to adjust the relative position of the surfaces of the two structures to set the predetermined and pre-set limit.

In one embodiment, the dose limiting sleeve is a tubular structure having a first open end and a second end opposite the first open end. One of the two structures is positioned within the first open end of tubular structure. This structure includes a set of grooves and the dose limiting sleeve tubular structure includes a set of rails. The sets of grooves and rails rotationally couple the one of the two structures and the dose limiting sleeve tubular structure so that the one of the two structures and the dose limiting sleeve tubular structure rotate together. The set of grooves and the set of rails are illustrative of a first rotational interlocking structure and a second rotational interlocking structure, respectively, wherein the interaction of the first and second rotational interlocking structures rotationally couples the two parts containing the first and second rotational interlocking structures.

As mentioned above, one of the plurality of assemblies of the medicament injection assembly is a variable dosing assembly movably coupled to the automatic dosing assembly, and having a first end. The variable dosing assembly is selectively engaged by the user to dispense a predetermined and adjustable amount of a medicament from the medicament injection apparatus upon engagement and actuation of the medicament injection assembly.

Another one of the plurality of assemblies of the medicament injection assembly is a medicament cartridge assembly that is removably affixed to the first end of the variable dosing assembly, as described above. The medicament cartridge assembly has a first end and a second end opposite the first end. The second end is fashioned to accept a medicament cartridge having a first sealed end and a second end opposite the first sealed end which contains a movable plunger.

A needle subassembly is removably affixed to the first end of the medicament cartridge assembly, in one embodiment.

When the needle subassembly is in the first position, the needle is contained within the needle shroud, as explained above. Similarly, when the needle subassembly is in the second position, the needle has an end extending through the open end of the needle shroud. The needle safety cap is removably affixed to the medicament cartridge assembly so that the needle safety cap encloses the needle. Specifically, in one embodiment, a groove in an inner surface of the needle safety cap snaps over a radial lip of the medicament cartridge assembly.

As mentioned previously, the variable dosing assembly includes a pushrod subassembly and a dosing sleeve subassembly. The pushrod subassembly includes a pushrod that is used to engage the plunger and to moves the plunger in the first direction inside the medicament cartridge. The dosing sleeve subassembly is movably mounted on the pushrod. The dosing sleeve subassembly position on the pushrod determines how far the pushrod can move in the first direction, which in turn determines the dose injected by the medicament injection apparatus of this invention.

In addition to the various assemblies and subassemblies described above, the medicament injection assembly includes a runner having a first tubular portion and a second tubular portion. The first tubular portion has a first open end and a second open end opposite the first open end. The second open end of the first tubular portion is coupled to a first open end of the second tubular portion and the second tubular portion has a second open end opposite the first end.

The dosing sleeve subassembly of the variable dosing assembly is partially positioned within the first open end of the first tubular portion of the runner such that the dosing sleeve subassembly can move back and forth in both the first direction and the second direction within the first tubular portion of the runner. The second tubular portion of the runner has a smaller cross-section than a cross-section of the first open end of the tubular dose knob so that at least part of the second tubular portion of the runner is positioned inside the first open end of the tubular dose knob and the second tubular portion can move back and forth in both the first direction and the second direction within the tubular dose knob.

In one embodiment, the second tubular portion of the runner includes a set of grooves and the tubular dose knob includes a set of rails. The set of grooves and rails rotationally couple the runner and the tubular dose knob so that the runner and the tubular dose knob rotate together to move the dosing sleeve subassembly back and forth in both the first direction and the second direction within the first tubular portion of the runner. Thus, this action adjusts the amount of medicament dispensed from the medicament injection apparatus.

In this embodiment, the first open end of the second tubular portion of the runner contains one end of the pushrod along with the attached trust bearing. Thus, the pushrod effectively closes the first end of the second tubular portion. The second end of the tubular dose knob is also closed. The second tubular portion of the runner with the pushrod and the tubular dose knob form an enclosed cavity with a variable length which is smaller when the plurality of assemblies of the medicament injection assembly are in the first position and larger when the plurality of assemblies are in the second position.

The pushrod and the runner are coupled so that when the plurality of assemblies are in the first position the pushrod and the runner are removably affixed and when the plurality of assemblies move from the first position to the second position the pushrod and the runner remain removably affixed and move together a predetermined distance in the first direction. The pushrod is uncoupled from the runner once the pushrod and the runner have moved together the predetermined distance. Therefore, the pushrod can move forward, independently of the runner, past the predetermined distance in the first direction.

The motive force subassembly is positioned inside the cavity such that the motive force subassembly exerts a force on the pushrod and, therefore the runner, in the first direction and the motive force subassembly exerts a force on the tubular dose knob in the second direction when the plurality of assemblies are in the first position.

The thrusting assembly, described above, also includes a lock ring that selectively engages and holds the tubular dose knob against the force exerted in the second direction, and a needle thrust locking mechanism that selectively engages and holds the runner, and therefore the pushrod, against the force exerted in the first direction. The motive force subassembly comprises a spring and a thrust bearing.

The above embodiment is illustrative of only the principles of this invention. Those skilled in the art will appreciate that a variety of novel medicament injection apparatuses can be formed using various combinations of the novel assemblies and subassemblies of this invention. For example, if a maximum permissible dose is not of concern, only the thrusting assembly of the automatic dosing assembly would be utilized. The resulting medicament injection apparatus provides manually adjustable doses by simply turning the dose knob, for example, three complete revolutions would be one dose and four complete revolutions another dose. This simple dose adjustment combined with the motion provided by the thrusting assembly allows accurate and reliable injections in a wide variety of situations including low light or use by a blind person.

BRIEF DESCRIPTION OF THE DRAWINGS

FIG. 7E is an enlarged perspective view of an alternate embodiment of the angled cylinders of FIGS. 7C and 7D including stepped angled cylinders.

FIG. 7F is a side view of the stepped angled cylinders of FIG. 7E.

In the figures, like components are designated by like reference numerals throughout.

DETAILED DESCRIPTION

Figure 2:
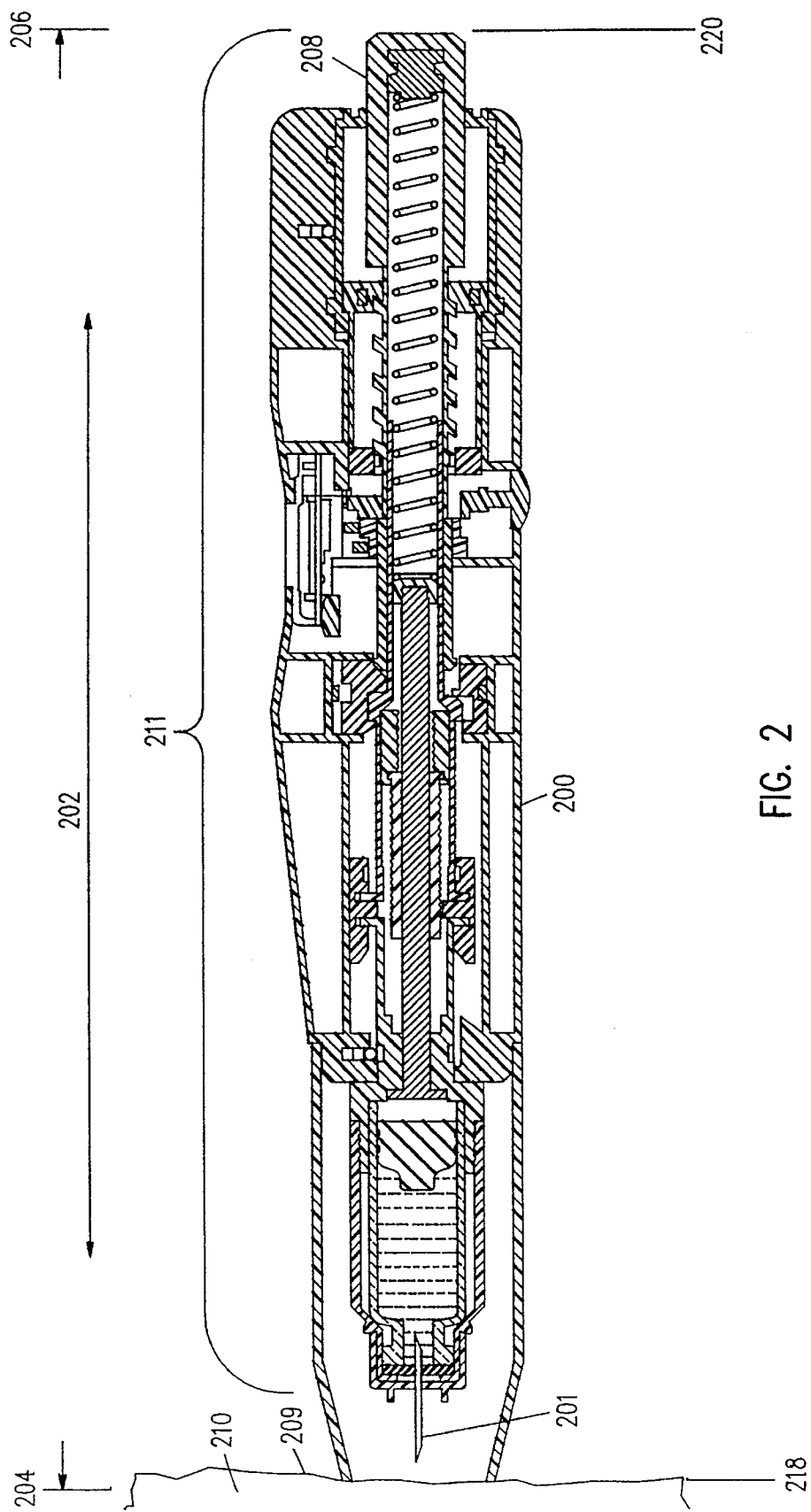
FIG. 2 is an enlarged, front elevation view, in cross section, of a medicament injection apparatus constructed in accordance with the present invention.

According to the principles of this invention, a medicament injection apparatus 200, such as is shown in cross-section, front elevation view in FIG. 2, automatically administers a predetermined dose of a medicament, sometimes called a pre-set dose, for either a subcutaneous or intramuscular injection when the patient activates a dose knob 208 which is located at back 220 of medicament injection apparatus 200. Upon activation, a medicament injection assembly 211 of medicament injection apparatus 200 supplies a motive force which moves a plurality of assemblies of medicament injection assembly 211 along an axis 202 in a forward direction 204 towards front 218 of medicament injection apparatus 200 and a pre-sterilized needle 201, also referred to as needle 201, is projected beyond front 218 of medicament injection apparatus 200 through the patient's skin 209 and into the tissue 210 where the pre-set dose is administered.

Figure 1:
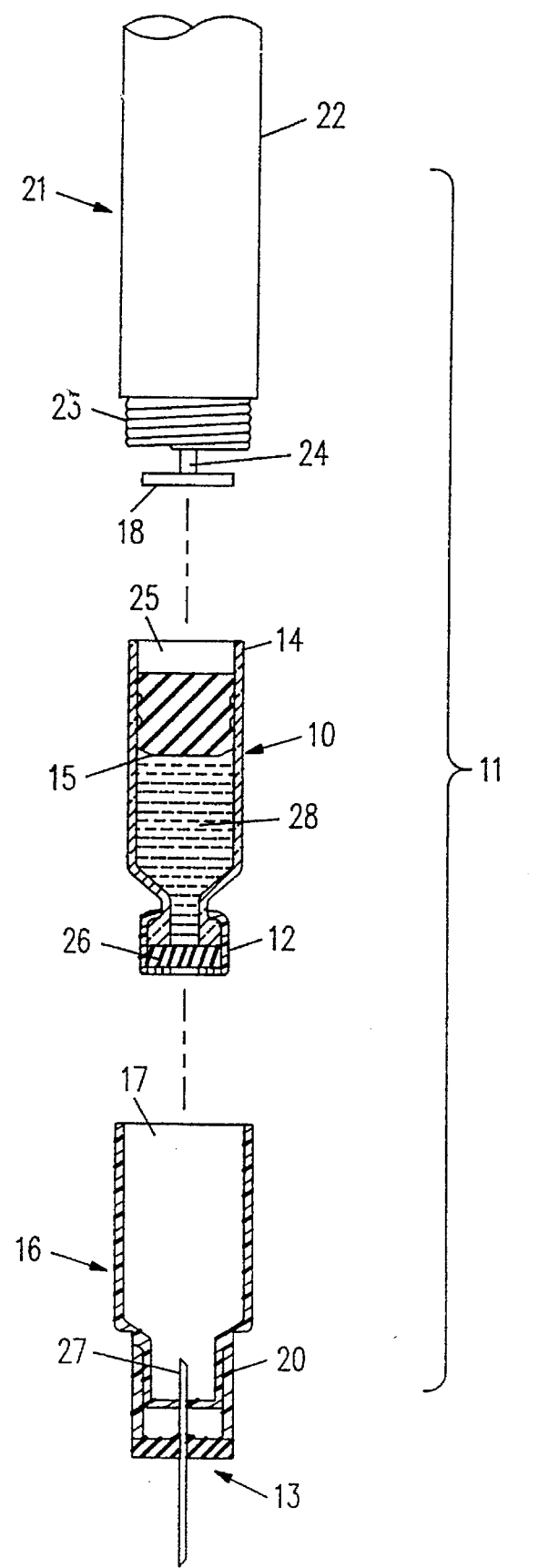
FIG. 1 is an exploded, fragmentary, front elevation view, in partial cross-section, of a prior art injection pen device.

The structure of medicament injection apparatus 200 hides needle 201 from the user and at the same time assures that needle 201 is oriented substantially perpendicular to the patient's skin 209. Consequently, the likelihood of an ineffective injection is dramatically reduced in comparison to prior art medicament injection apparatus 11 (FIG. 1). Moreover, as explained more completely below, administration of pre-set doses does not require manipulation of any complex mechanisms. Rather, the user simply reactivates medicament injection assembly 211 and then depresses dose knob 208. Medicament injection apparatus 200 is designed so that the reactivation of medicament injection assembly 211 can be accomplished in .any situation by a child, adult or even a blind child or adult.

Figure 3:
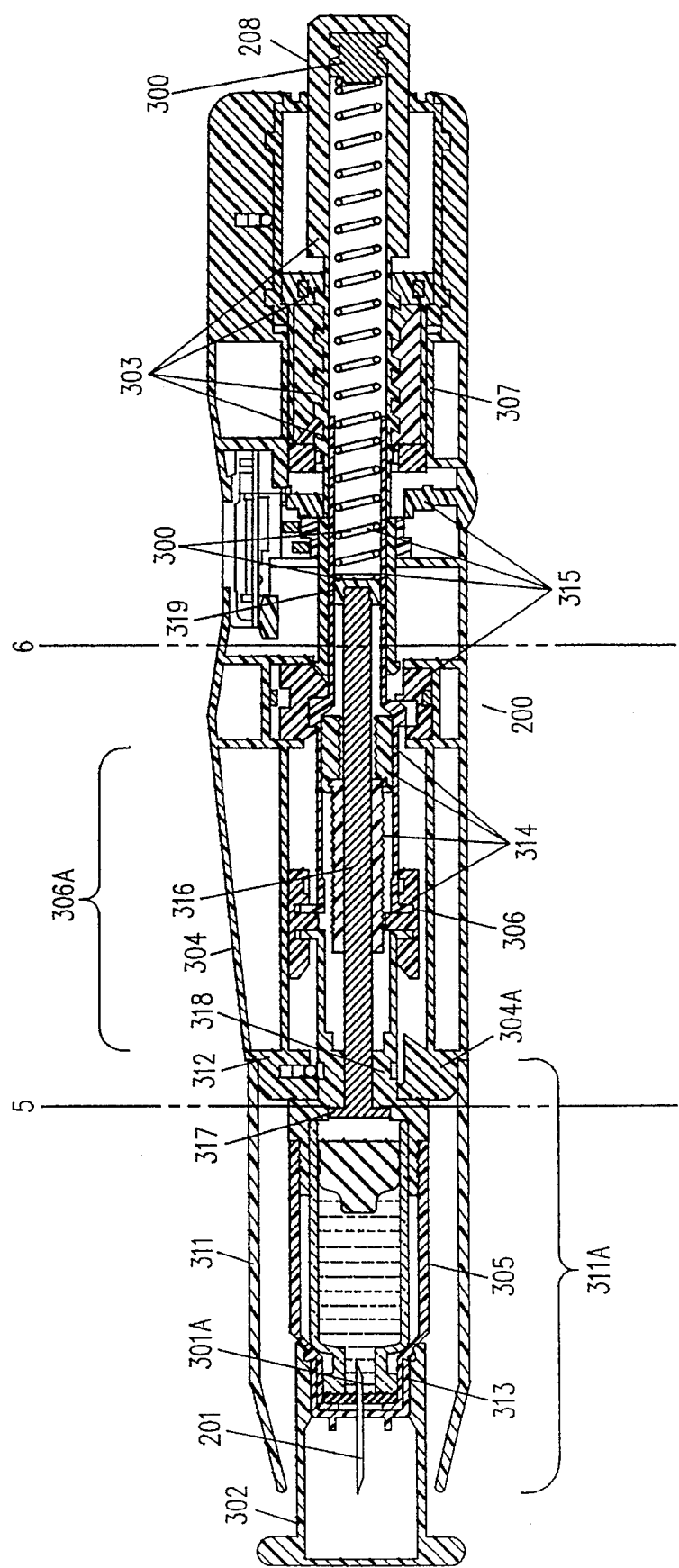
FIG. 3 is an enlarged, front elevation view, in cross section, of a medicament injection apparatus constructed in accordance with the present invention along with lines 5 and 6 which divide the medicament injection apparatus into the three sections detailed in FIGS. 5A–7J.

FIG. 3 is an enlarged, front elevation view, in cross section, of medicament injection apparatus 200 including: needle 201, needle safety cap 302, housing 304 with needle shroud 311 and mounting structures 312, 304A, medicament cartridge assembly 305 with end 313, variable dosing assembly 306 with pushrod subassembly 306A and dosing sleeve subassembly 314, dose knob 208, and automatic dosing assembly 307 with dose knob stop assembly 303 and thrusting assembly 315. Each of these assemblies is described more completely below.

Housing 304 encloses medicament injection assembly 211 which includes medicament cartridge assembly 305, variable dosing assembly 306 and automatic dosing assembly 307. Housing 304 provides various mounting structures 312 which hold assemblies 305, 306, 307 in position with respect to each other. Housing 304 also includes needle shroud 311 that is mounted on needle shroud seat 304A. Needle shroud 311 surrounds medicament cartridge assembly 305 and hides needle 201 from view when medicament injection apparatus 200 is in the "energized", e.g., retracted condition. Needle safety cap 302 protects needle 201 and snaps over end 313 of medicament cartridge assembly 305.

Medicament cartridge assembly 305 contains a medicament. The medicament is usually a solution. Pre-sterilized needle 201 that is, in this embodiment, a double sided and double grind variety, is affixed to medicament cartridge assembly 305 so that one end 301A of needle 201 is in communication with the medicament.

Variable dosing assembly 306 interacts with medicament cartridge assembly 305 through pushrod subassembly 306A which includes pushrod 316 with pushrod piston head 317, and cartridge seat 318. Dosing sleeve subassembly 314 controls the amount of medicament dispensed by controlling the distance pushrod 316 moves forward. The dose delivered is set by manipulation of dose knob 208.

Pushrod subassembly 306A also interacts with automatic dosing assembly 307. Automatic dosing assembly 307 performs two functions. First, through motive force subassembly 300 of thrusting assembly 315, assembly 307 provides the force necessary to move variable dosing assembly 306, with pushrod subassembly 306A, and medicament cartridge assembly 305 forward when medicament injection apparatus 200 shifts from the "energized" e.g. retracted position, to the "activated" e.g. extended, position. This shift, also called "needle thrust activation" is controlled by thrusting assembly 315 and powered by motive force subassembly 300. Needle trust activation causes needle 201 to extend outside needle shroud 311, penetrate skin 209, and enter the patient's tissue 210. Second, automatic dosing assembly 307 also delivers a pre-set dose by a simple manipulation of dose knob 208 which interacts with dose knob stop assembly 303 to control the pre-set dose.

Automatic dosing assembly 307 also includes, in one embodiment, a safety mechanism that prevents changing the pre-set dose without a special wrench or tool. Until the pre-set dose is changed with this tool by the doctor or a trained patient, the dose remains at the pre-set level so that medicament injection apparatus 200 can be quickly picked up and the proper dose administered with minimal patient/user manipulation. This pre-set dose also serves as a maximum allowable dose when manual variable doses are desired. The process of setting the automatic dose is described in detail below.

Figure 4:
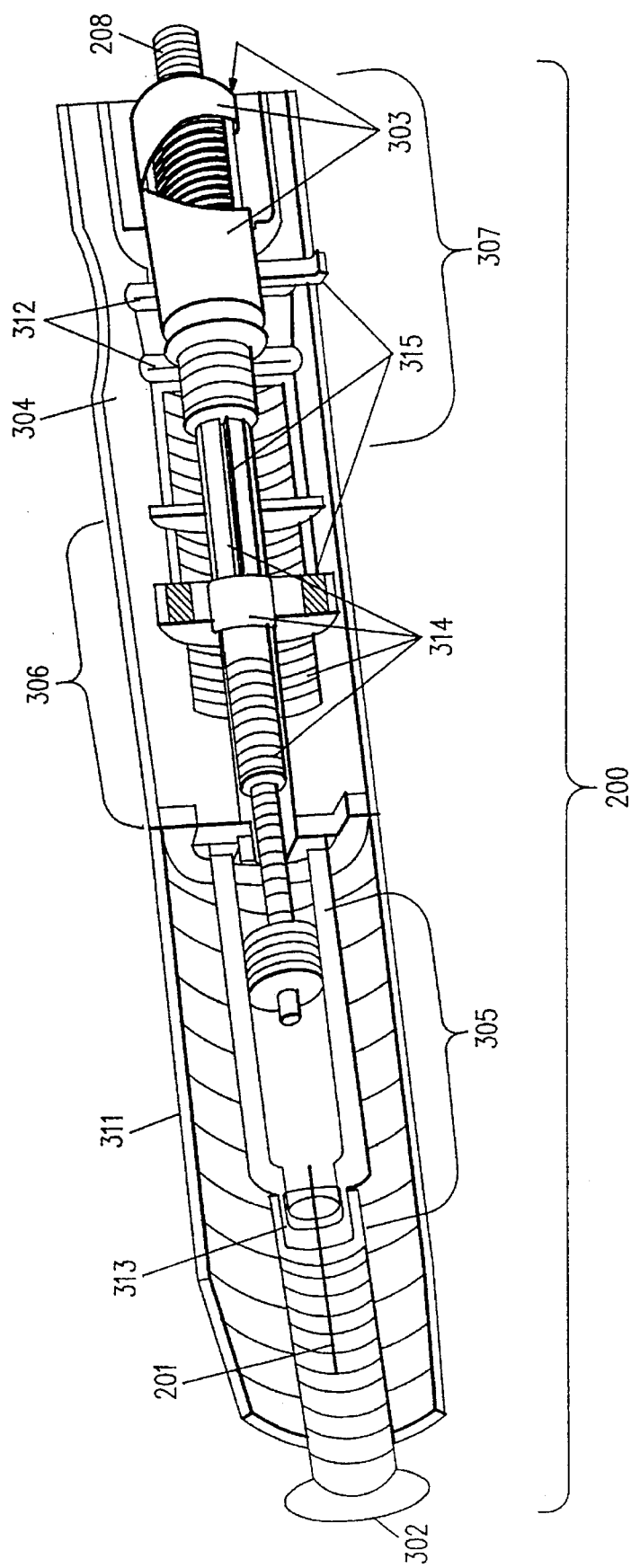
FIG. 4 is an angled cut away view of the medicament injection apparatus of FIG. 3.

FIG. 4 is an angled cut away of medicament injection apparatus 200 showing a perspective view of medicament injection apparatus 200 and the relative positioning and interaction of some of the major components of FIG. 3.

To administer a pre-set dose of the medicament, the patient (i) energizes medicament injection apparatus 200; (ii) removes needle safety cap 302; (iii) places needle shroud 311 of housing 304 at the location where the injection is desired; and (iv) engages dose knob 208. When the patient engages dose knob 208, variable dosing assembly 306 and medicament cartridge assembly 305 are moved by thrusting assembly 315 and motive force subassembly 300 so that needle 201 is thrust beyond needle shroud 311 through the patient's skin 209 and into tissue 210. Variable dosing assembly 306 then allows a predetermined dose of medicament to pass from medicament cartridge assembly 305 through needle 201 into the patient.

By simply engaging dose knob 208, the patient causes needle 201 to project outside needle shroud 311, and to be introduced into the patient's tissue 210. An accurate pre-set dose is then automatically dispensed in the patient's tissue 210. With medicament injection apparatus 200, the patient can ensure approximately perpendicular needle/skin alignment simply by placing needle shroud 311 firmly against the injection site. The patient is not required to manually introduce the needle into his or her tissue 210. This decreases the trauma for the patient, and increases the likelihood that the patient will continue to administer treatment.

Even in cases where a child is to too young to self administer the injection, the role of a parent or guardian in administering treatment is far easier with medicament injection apparatus 200 than with prior art medicament injection apparatuses because needle 201 is concealed from the child prior to injection. This novel feature of the present invention helps the child develop a more positive attitude towards the treatment. Once the child is old enough to self administer his or her own injection, this positive attitude can help ensure a continued compliance with the treatment and result in a happier and healthier adult patient.

Further, as described above, in the present invention, the pre-set dose can be delivered at any time by simply energizing medicament injection apparatus 200, as described below, and then engaging dose knob 208. Due to its simplicity of use, medicament injection apparatus 200 is particularly well suited for children and those with permanent or temporary disabilities. It is also ideal for emergency use in life-threatening situations such as epinephrine treatment for allergic reactions to bee stings and antidotes for nerve agents on the battlefield. In these situations time is of the essence and the patient may be too pressured or incapacitated to give proper attention to a standard dose meter.

Medicament Cartridge Assembly

Figure 5A:
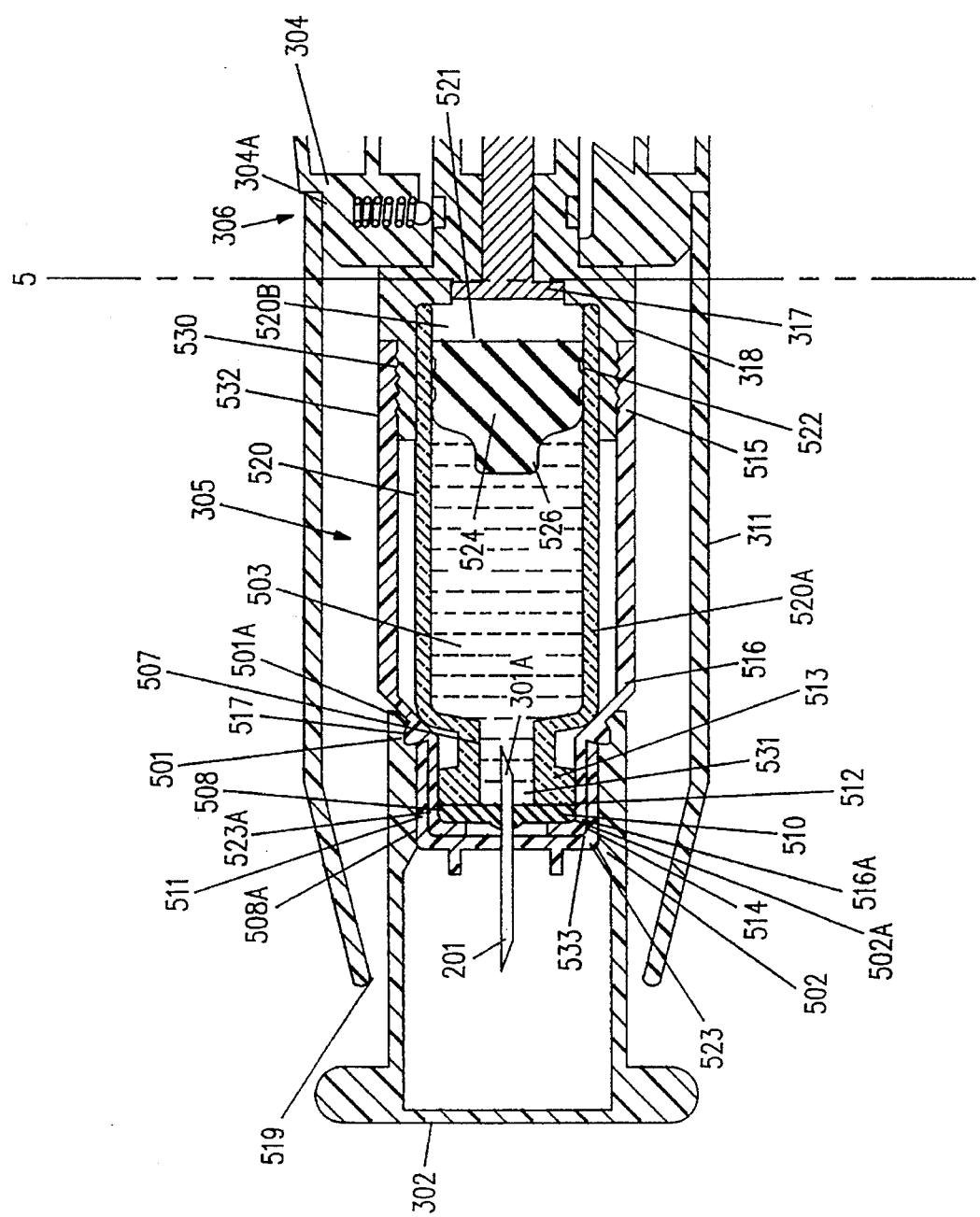
FIG. 5A is an enlarged, fragmentary, front elevation view, in cross section, of a portion of an medicament injection apparatus constructed in accordance with the present invention including the medicament cartridge assembly.

FIG. 5A is an enlarged cross section of medicament cartridge assembly 305 of FIG. 3. Medicament cartridge assembly 305 includes a needle subassembly 508 (FIG. 5B) that is removably affixed to cartridge housing 516. A medicament cartridge 520 that contains medicament 503 and a plunger 524 is secured within cartridge housing 516 by a cartridge seat 318 of pushrod subassembly 306A of variable dosing assembly 306. Each of these components is described more completely below.

The body of medicament cartridge 520 is a glass container 520A, sometimes called "a vial," which is made from type 1 borosilicate glass of 9.6 DIN.

A plunger 524 having integral fluid barrier rings 522 is inserted into open end 520B of vial 520A. Additionally, plunger 524 is formed with a fitted tip 526 which serves to expel a maximum amount of medicament 503 from neck 507 of vial 520A. Specifically, fitted tip 526 is designed to extend into neck 507 of vial 520A so that fitted tip 526 is a selected distance from end 301A of needle 201. Plunger 524 is made of butyl rubber or some other form fitting material.

Pushrod piston head 317 of pushrod subassembly 306A of variable dosing assembly 306, as explained more completely below, contacts plunger 524 at plunger base 521. Thus, when pushrod piston head 317 is moved towards needle 201, plunger 524 is moved towards needle end 301A and consequently forces medicament 503 through needle 201.

Lined seal subassembly 511 includes a natural rubber seal 510 mounted adjacent to and in contact with a butyl rubber seal 512. Lined seal subassembly 511 is held against open end 531 of vial 520A by aluminum seal 514 so that butyl rubber seal 512 contacts and seals open end 531. In this embodiment, vial 520A has a lip 513 so that aluminum seal 514 can positively engage vial 520A and hold lined seal 511 in place. Vial 520A, lined seal 511, and aluminum seal 514 are similar to those used in prior art medicament injection apparatuses. Further, pre-filled medicament cartridges 520 are well known in the art and are commercially available from various manufactures depending on the medicament contained. Additionally, it is possible to refill medicament cartridge 520 with medicament 503 using techniques well known by those skilled in the art.

Medicament cartridge 520 is positioned within cartridge housing 516. Cartridge housing 516 is made of aluminum, steel or some other high tensile strength material. One end 532 of cartridge housing 516 has threads 530 on its interior surface which couple cartridge housing 516 to a cartridge seat 318 of pushrod subassembly 306A via complementary threads 515 on cartridge seat 318. Thus, medicament cartridge assembly 305 is removably affixed to variable dosing assembly 306 by the interaction of threads 530 with threads 515.

The coupling of cartridge seat 318 and cartridge housing 516 secures medicament cartridge 520 in place and connects medicament cartridge assembly 305 to the other assemblies in medicament injection apparatus 200. Also, cartridge housing threads 530 and cartridge seat threads 515 permit removal of medicament cartridge assembly 305 from cartridge seat 318 and thereby allow for replacement of medicament cartridge 520 once medicament 503 has been exhausted. Cartridge seat 318 can be made from several suitable materials such as metal or plastic.

End 533 of cartridge housing 516 has a radial lip 517 which allows for attachment and detachment of needle safety cap 302, that is described more completely below. Needle subassembly 508 is removably mounted to end 533 of cartridge housing 516. Needle subassembly 508 includes needle 201 that is pre-sterilized and is mounted in a cartridge housing cap 523, which is plastic, in this embodiment. Cap 523 is secured to cartridge housing 516 by mating threads on inside surface 523A of cap 523 with threads on exterior surface 516A of cartridge housing 516. Needle 201 is, in one embodiment, a 27 gage (0.36 millimeter) or smaller diameter, micro-fine, double grind and double sided needle. When cap 523 is affixed to cartridge housing 516, double grind and double sided needle 201 pierces lined seal subassembly 511 and is in communication with medicament 503.

Needle safety cap 302 is a plastic cap, which upon mounting to cartridge housing 516, protects needle 201 and prevents accidental punctures by enclosing needle 201. Needle safety cap 302 fits inside open end 519 of needle shroud 311 and snaps over radial lip 517. Needle safety cap 302 must be removed prior to injection. Further, as described in detail below, needle safety cap 302 must be capable of transferring a force sufficient to energize medicament injection apparatus 200.

In this embodiment, an inner cylindrical surface 502 of needle safety cap 302 contacts an outer cylindrical surface 508A of cap 523 of needle subassembly 508. Inner cylindrical surface 502 of needle safety cap 302 has grooves 502A which couple with complementary grooves 523A (FIG. 5B) on surface 508A of cap 523 of needle assembly 508. This system of groove allows cap 523 to be removably attached on threads 516A of cartridge housing 516 without removing needle safety cap 502. A groove 501 is formed a selected distance from an end 501A of needle safety cap 302 in an inner cylindrical surface 502. The size of the groove and the position of the grove are selected to give a positive stable engagement when needle safety cap 302 is slid over radial lip 517 so that groove 501 mates with radial lip 517.

Needle shroud 311 is plastic, in this embodiment, and surrounds cartridge housing 516 when medicament injection apparatus 200 is in a "cocked" position, e.g., retracted, and in an "activated", e.g., extended, position. Additionally, needle shroud 311 surrounds needle 201 when medicament injection apparatus 200 is in the retracted position. However, as explained above, upon needle thrust activation of medicament injection apparatus 200, needle 201 projects outside open end 519 of needle shroud 311 to introduce needle 201 into tissue 210 (FIG. 2).

Needle shroud 311 fits onto housing 304 at needle shroud seat 304A (FIG. 3). Needle shroud 311 is removably attached to needle shroud seat 304A by way of a snug fit, thereby creating a friction mount. This allows removal of needle shroud 311. A removable needle shroud is desirable to allow access to cartridge housing 516 and to allow the doctor or patient to replace or exchange needle shroud 311.

Replacement of needle shroud 311 may be necessary because length 311A (FIG. 3) of needle shroud 311 determines the distance needle 201 projects outside open end 519 of needle shroud 311 and extends into tissue 210 (FIG. 2) upon needle thrust activation. The distance needle 201 extends into tissue 210 must be variable to accommodate different types of injections, e.g., intramuscular versus subcutaneous, and the varying size and age of patients. Therefore, needle shroud 311 is removably mounted to housing 304 and needle shrouds of various lengths 311A are contemplated. This allows the doctor and patient to select the proper shroud for the treatment and the patient's physical dimensions. Further, if the patient starts treatment as a child, new needle shrouds 311 can be purchased to adjust to the growing child rather than buying an entirely new injection pen 200. This fact could result in considerable cost savings.

Figure 5B:
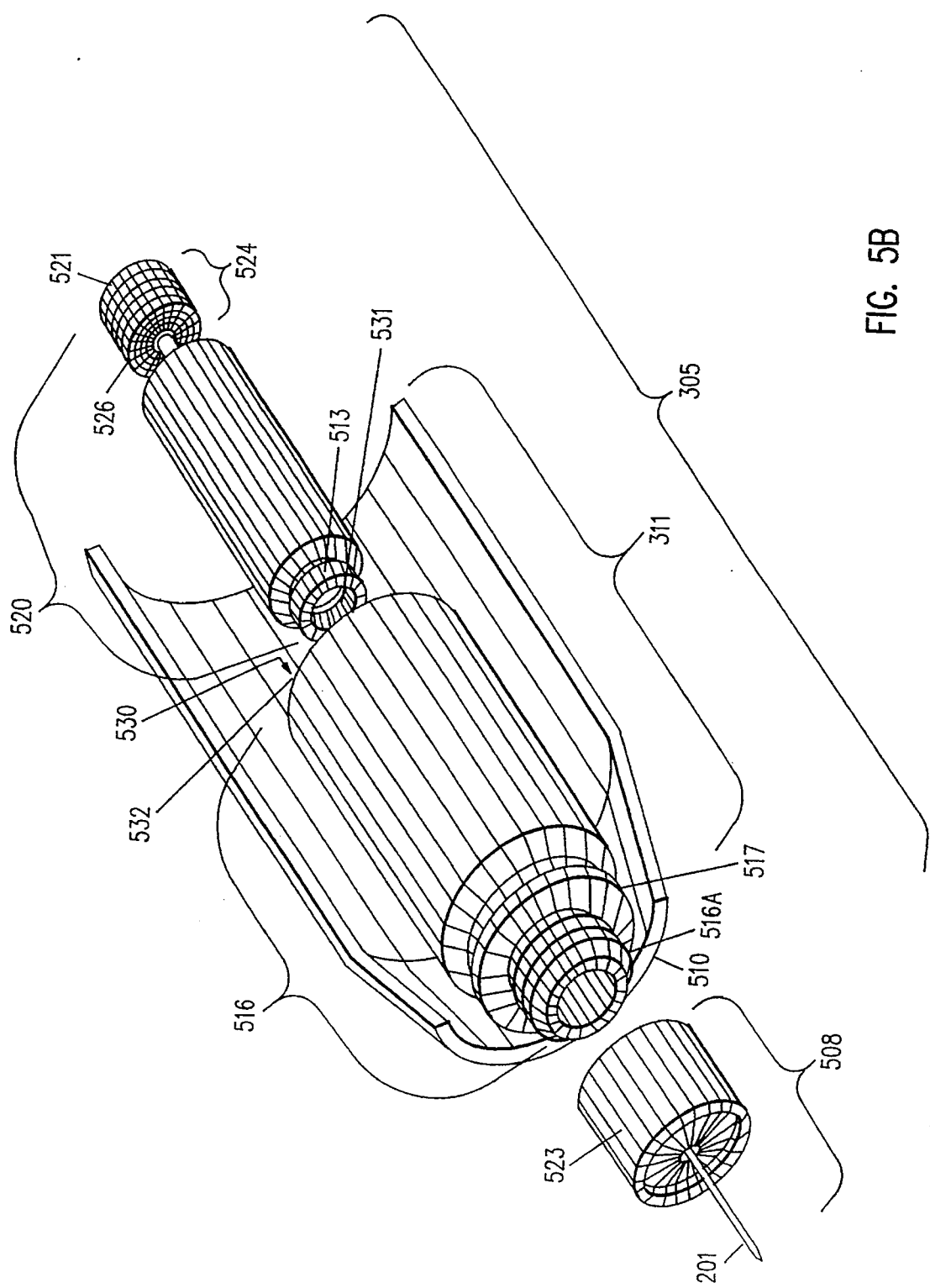
FIG. 5B is an exploded top perspective view of the portion of the medicament injection apparatus of FIG. 5A.

FIG. 5B is an exploded, top perspective view, of medicament cartridge assembly 305 that shows the interaction and relative positioning of some of the major parts of medicament cartridge assembly 305 including: medicament cartridge 520 with plunger 524, plunger fitted tip 526 and base 521, cartridge housing 516 with lip 517 for mounting needle safety cap 302 (FIG. 5A) and threaded exterior surface 516A for securing cap 523. It should be noted that because this is an exploded view, needle subassembly 508, cartridge housing 516, and medicament cartridge 520 appear outside needle shroud 311. However, in practice, these parts actually fit together and are positioned inside needle shroud 311 with the exception of needle 201 when medicament injection apparatus 200 is in the "activated", e.g. extended position. Also shown is cartridge housing end 532 which has threads 530 on its interior surface for securing cartridge housing 516 to cartridge seat 318. Vial lip 513 of medicament cartridge 520 for securing aluminum vial seal 514, and sealed end 531 of vial 520A are also shown.

An important aspect of this invention is that needle shroud 311 and needle safety cap 302 allow the patient to administer medicament directly into tissue 210 without seeing needle 201 prior to and during injection. This serves to minimize patient trauma and increases the probability that the patient will comply with the prescribed treatment.

Further, by placing open end 519 of needle shroud 311 firmly against skin 209, with needle safety cap 302 removed, the patient can ensure a perpendicular orientation between the needle point and skin 209. This helps ensure proper introduction of medicament into the tissue 210.

Those skilled in the art will recognize that many changes to the embodiment of medicament injection apparatus 200 described can be made without departing from the true spirit of the invention. For instance, the size of the medicament cartridge 520, relative to medicament injection apparatus 200, is merely illustrative and not limiting. Medicament cartridges 520 can have volumes ranging from fractions of milliliters to multiple milliliter units. To accommodate larger or smaller medicament cartridges 520, larger or smaller medicament cartridge assemblies 305 and pushrods 316, as well as needle shrouds 311, can be employed. The embodiment of medicament injection apparatus 200 and medicament cartridge assembly 305 described above is therefore only illustrative and it's relative proportions are not limiting.

Variable Dosing Assembly

Figure 6A:
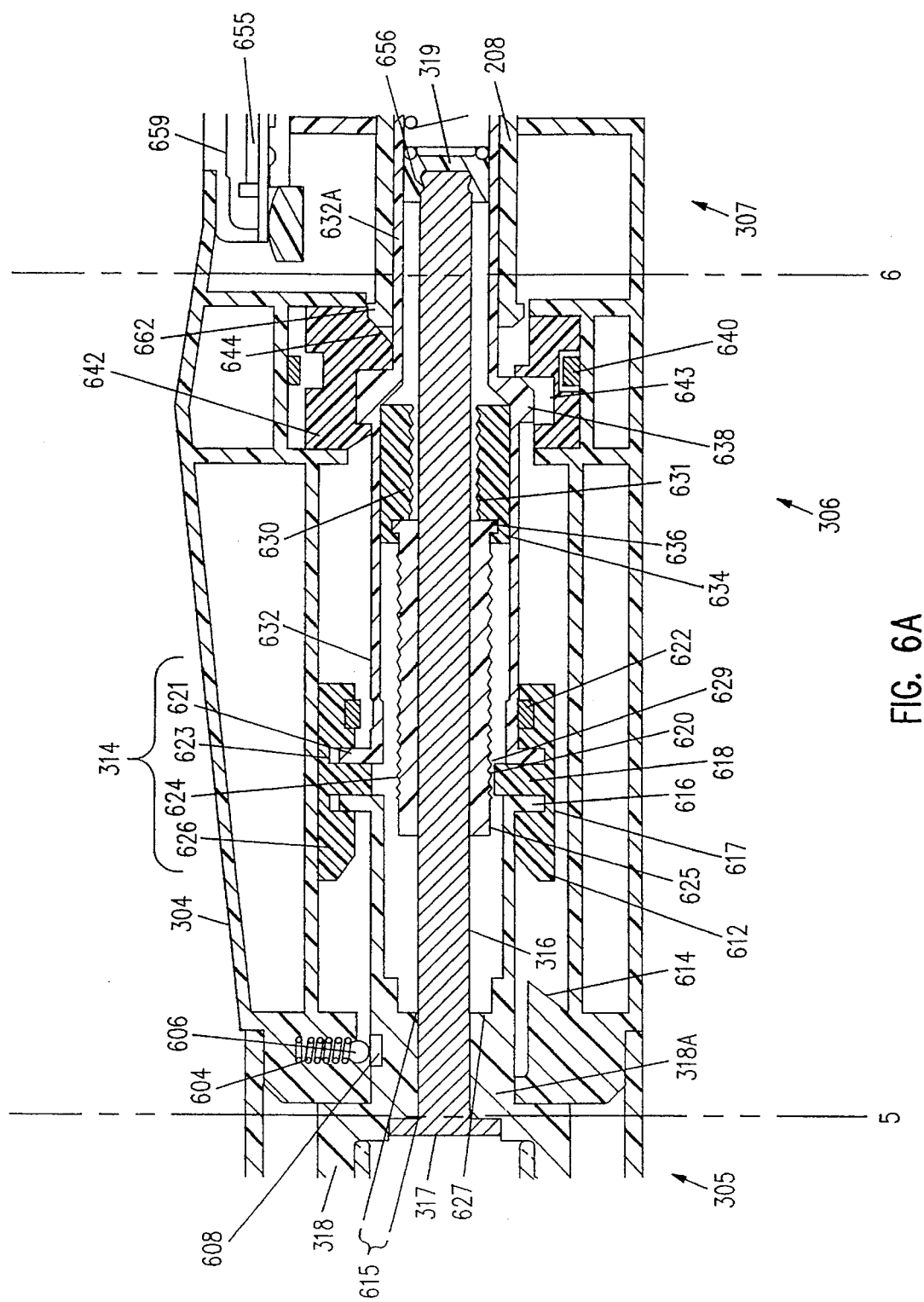
FIG. 6A is an enlarged, fragmentary, front elevation view, in cross section, of a portion of a medicament injection apparatus constructed in accordance with the present invention including the variable dosing assembly.

FIG. 6A is an enlarged, front elevation cross-sectional view of variable dosing assembly 306 (between lines 5 and 6 in FIG. 3) of medicament injection apparatus 200. Variable dosing assembly 306 includes two subassemblies; pushrod subassembly 306A (FIG. 3) and dosing sleeve subassembly 314. As explained above, pushrod subassembly 306A includes pushrod 316 with pushrod piston head 317 and cartridge seat 318 with neck 318A. Dosing sleeve subassembly 314 includes rachet sleeve 624, pushrod locking mechanism 626 and dose-setting sleeve 630. As explained more completely below, dosing sleeve subassembly 314 limits the range of motion of pushrod 316 along axis 202 (FIG. 2), and consequently the dose of medicament 503 delivered from medicament cartridge assembly 305 by medicament injection apparatus 200.

Figure 6B:
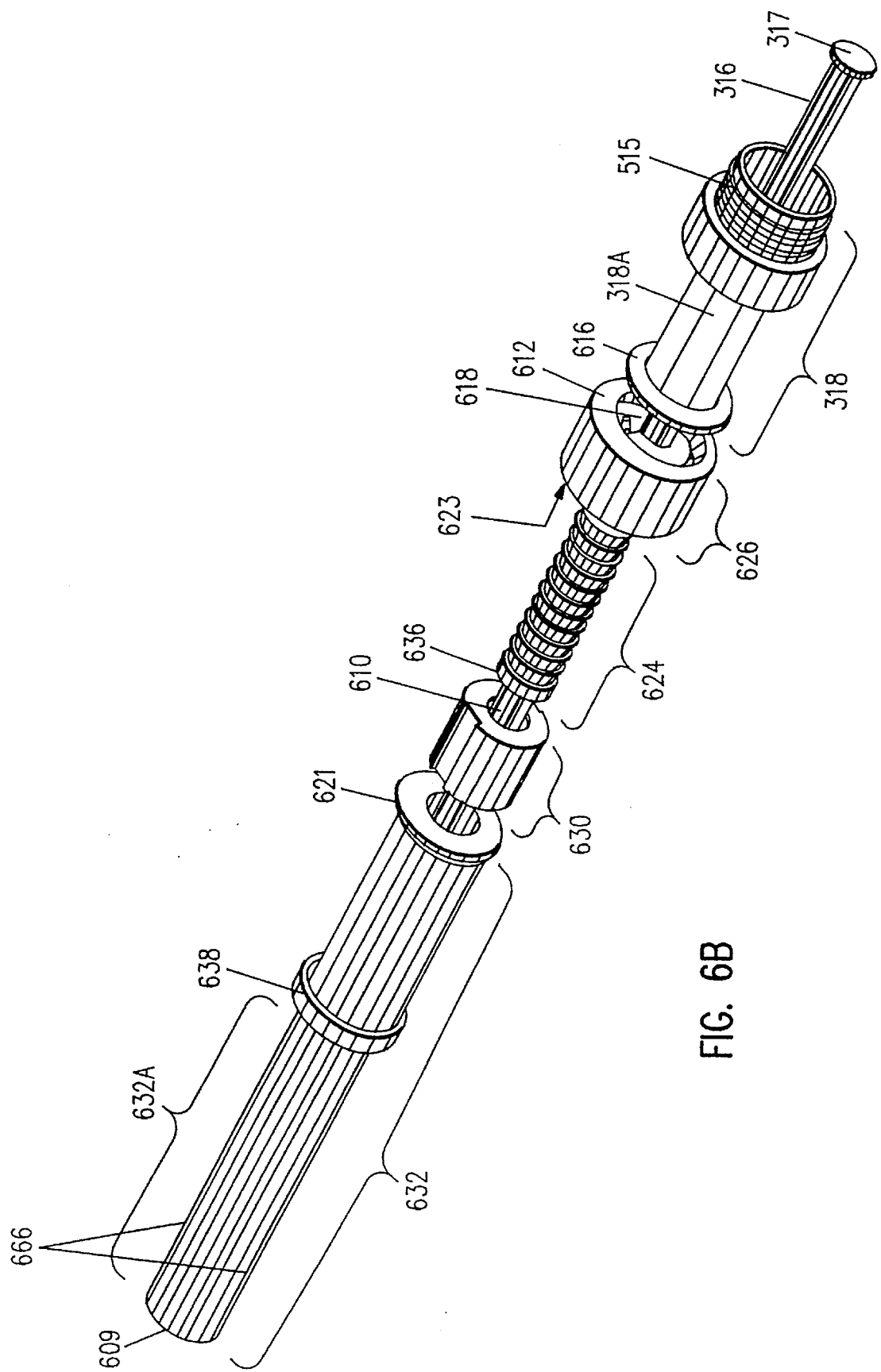
FIG. 6B is an exploded top perspective view of the cartridge seat, pushrod locking mechanism, rachet sleeve, dose-setting sleeve, and runner of FIG. 6A.
Figure 6C:
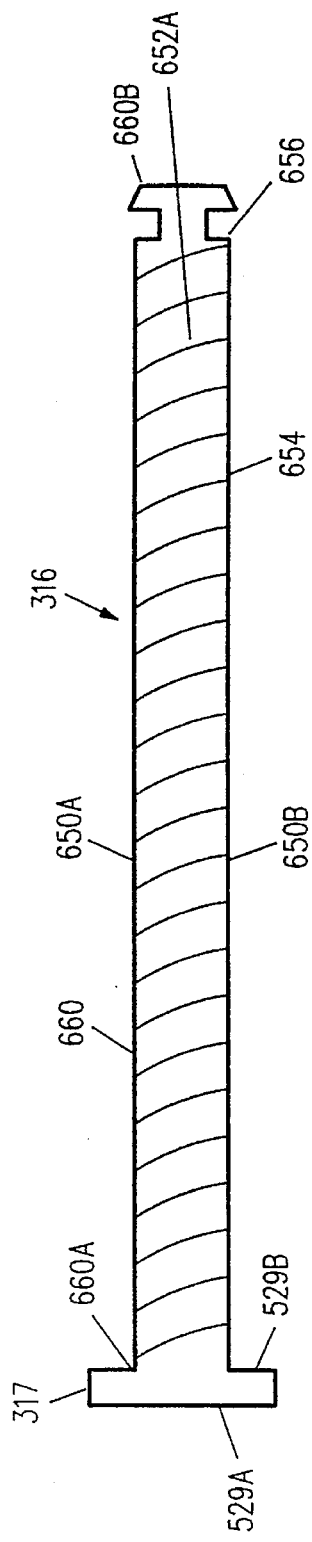
FIG. 6C is an enlarged, side view of the pushrod, with pushrod piston head, of FIG. 6A.
Figure 6E:
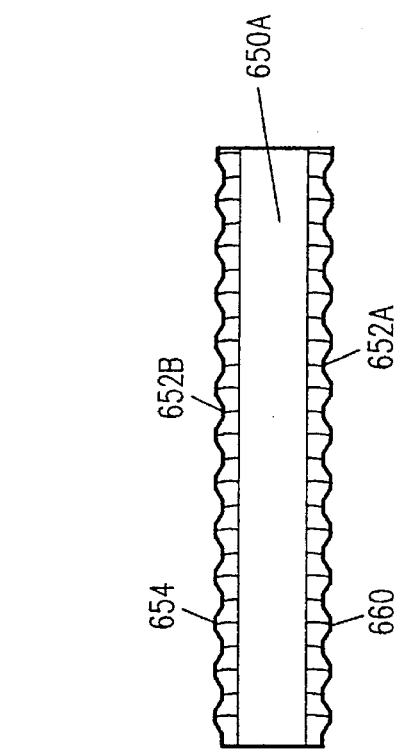
FIG. 6E is an enlarged, top view of a portion of the pushrod of FIG. 6C.
Figure 6D:
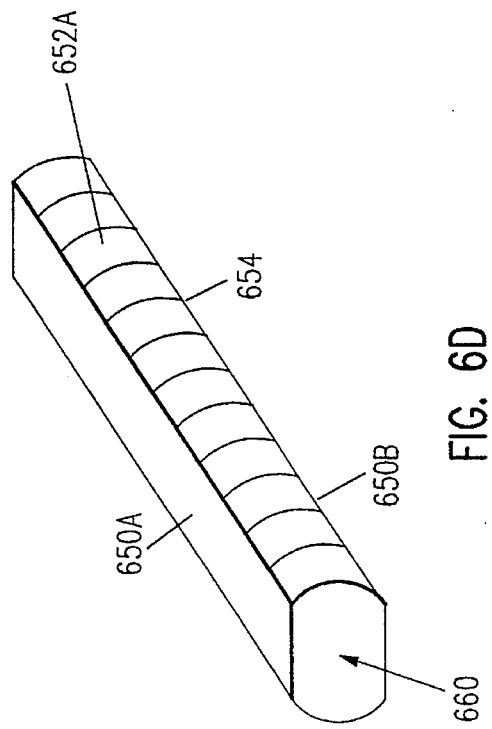
FIG. 6D is an enlarged, perspective view of a portion of the pushrod of FIG. 6C.

FIG. 6B is an exploded top perspective view of cartridge seat 318, pushrod locking mechanism 626, rachet sleeve 624, dose-setting sleeve 630, and runner 632. Pushrod 316 of pushrod subassembly 306A is shown in detail in FIGS. 6C, 6D and 6E. FIG. 6C is a side view of pushrod 316. FIG. 6D is a perspective top view of pushrod body 660 and FIG. 6E is a top view of pushrod body 660.

Pushrod piston head 317 is a circular disc having a flat surface 529A and a surface 529B, that is opposite flat surface 529A and is affixed to a first end 660A of pushrod 316. Pushrod body 660 has two opposed flat parallel surfaces 650A and 650B that are connected by circular arc surfaces 652A and 652B to form the shape shown in FIG. 6D. In this embodiment, circular arc surfaces 652A, 652B are threaded from just above pushrod piston head 317 to about radial groove 656. Specifically, circular arc surfaces 652A, 652B, that are sometimes called rounded surfaces 652A, 652B, each have fine right hand threads 654 that are selected so that the threads couple with threads 631 of dose-setting sleeve 630 that is described more completely below. Radial groove 656 near end 660B of pushrod rod body 660 is sized to permit attachment of thrust bearing 319 to pushrod 316. Pushrod 316 and pushrod piston head 317 are made of metal or another high tensile strength material.

Cartridge seat 318 is also a part of pushrod subassembly 306A. Pushrod 316 runs through neck 318A of cartridge seat 318. Cartridge seat neck 318A has a shape such that it contacts only flat surfaces 650A, 650B of pushrod 316. This permits pushrod 316 to move smoothly through cartridge seat neck 318A, and at the same time prevents pushrod 316 from rotating. Moreover, the axial contact length 615 between cartridge seat neck 318A and pushrod 316 is selected such that cartridge seat neck 318A acts as a guide bearing. This helps maintain the motion of pushrod 316 along axis 202 (FIG. 2) of injection pen 200 and so prevents jamming of plunger 524 in vial 520A.

Cartridge seat 318 terminates in a radial ring 616, that is sometimes referred to as "lip 616" which fits into a corresponding groove 617 of a pushrod locking mechanism 626, that is described below. This configuration ensures cartridge seat 318 is secured in the proper position and travels axially in unison with pushrod locking mechanism 626.

Ball and detent system 604, 606, 608 is positioned within housing 304 to prevent rotation and back threading of pushrod 316 into dose-setting sleeve 630 and to prevent rotation and back threading of cartridge seat 318 from cartridge housing 516. Coil spring 604 exerts a force on ball 606 which in turn exerts pressure on detent 608 in cartridge seat 318, thereby preventing cartridge seat 318 from rotating.

Rachet sleeve 624 is, in this embodiment, part of dosing sleeve subassembly 314, which also includes pushrod locking mechanism 626 and dose-setting sleeve 630. Rachet sleeve 624 surrounds a portion of pushrod 316. The position of rachet sleeve 624 on pushrod 316 controls the dose of medicament 503 injected. This is because when end region 625 of rachet sleeve 624 contacts rachet sleeve stop 627 of cartridge seat 318, the forward motion of pushrod 316 is stopped. Thus, the position of the rachet sleeve 624 on pushrod 316 controls how far pushrod 316 is displaced along axis 202 (FIG. 2) which, in turn, controls how far plunger 524 moves within vial 520A which, in turn, controls the amount of medicament 503 displaced through needle 201.

The length of rachet sleeve 624 represents the limit of pushrod 316 travel for each dose. When rachet sleeve 624 is positioned as close to end 660B (FIG. 6C) of pushrod 316 as possible, pushrod 316 will travel the maximum distance along axis 202, in forward direction 204 (FIG. 2) after needle thrust activation. Thus, rachet sleeve 624 determines the theoretical maximum dose. In one embodiment this theoretical maximum dose is the entire contents of medicament cartridge 520. However, in practice, as described in detail below, the maximum dose allowable is actually set by automatic dosing assembly 307 and in particular dose knob stop assembly 303.

Rachet sleeve 624 (FIG. 6A) also has rachet sleeve teeth 629 formed in its outer surface that extend from end region 625 to a predetermined distance from radial lip 636. There are complimentary rachet interlock teeth 620 on rachet interlock portion 618 of pushrod locking mechanism 626 that engage rachet sleeve teeth 629 under certain conditions. Specifically, in the stable condition, such as when medicament injection apparatus 200 is "cocked", metal ring spring 622 holds pushrod locking mechanism 626 so that rachet interlock teeth 620 engage rachet sleeve teeth 629 on rachet sleeve 624. Pushrod locking mechanism 626 thus holds rachet sleeve 624, and therefore pushrod 316 in position relative to runner 632 and cartridge seat 318. As explained below, this results in pushrod 316, locking mechanism 626, cartridge seat 318 and runner 632 moving forward as a single unit upon needle thrust activation. As also explained in more detail below, pushrod locking mechanism 626 maintains this interlocked position, via ring spring 622, until pushrod locking mechanism tapered edge surface 612 contacts housing 304 tapered cam portion 614, when this occurs pushrod 316 is freed to move forward independently of locking mechanism 626 and runner 632 and cartridge seat 318. This happens when medicament injection apparatus 200 shifts from the cocked position to the extended or activated position.

Rachet sleeve 624 is coupled to dose-setting sleeve 630 by a radial lip 636 that fits in a grove 634 within dose-setting sleeve 630. The position of rachet sleeve 624, and therefore the dose administered is adjusted by the interaction of dose knob 208 with variable dosing assembly 306 through runner 632 as described below.

Dose knob 208 is plastic, tubular and hollow (FIG. 7B) in this embodiment. One portion 632A (FIG. 6B) of runner 632, that is also plastic, tubular and hollow, has an outer diameter slightly smaller than the inner diameter of dose knob 208 allowing portion 632A of runner 632 to sit inside dose knob 208. The end of dose knob 208 inside which portion 632A of runner 632 sits has a beveled lip 662, the use of which is described more completely below.

According to the principles of this invention, runner 632 and dose knob 208 are shaped so that runner 632 can freely slide, e.g., "telescope," up and down, inside of dose knob 208 along axis 202. However, the two parts cannot rotate independently of each other. This rotational communication between dose knob 208 and runner 632 can be accomplished in one of several ways, two of which are illustrated in FIGS. 6F, 6G, and 6H.

In one embodiment, dose knob 208 (FIG. 6F) has two axial rails 664 extending from its inner surface. Axial rails 664 couple with complementary axial grooves 666 in the outer surface of portion 632A of runner 632 that extends from end 609 (FIGS. 6B and 6F) to runner lip 638 (FIG. 6B). In this configuration, tubular portion 632A is free to "telescope" back and forth inside dose knob 208, but runner 632 is interlocked in rotational motion with dose knob 208 by the interlocking of axial rails 664 in axial grooves 666.

Figure 6G:
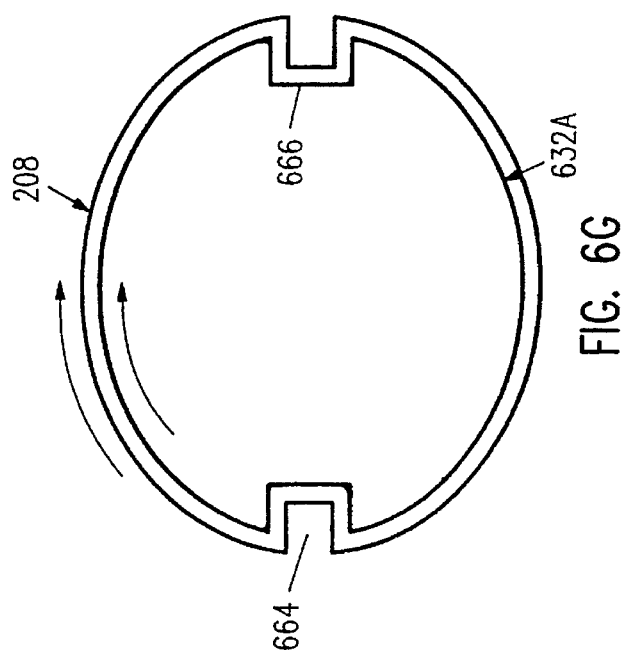
FIG. 6G is an enlarged, cross-sectional view, of the interface between the dose knob and runner of FIGS. 6A and 6B showing detail of the rail and groove rotational interlock.
Figure 6H:
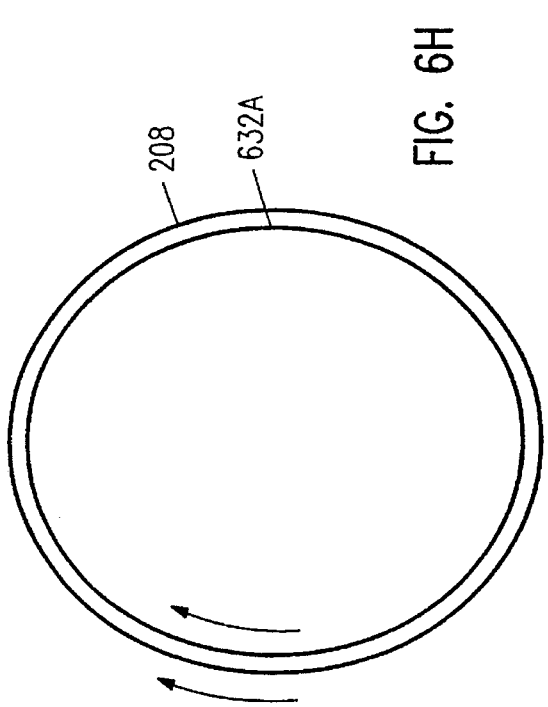
FIG. 6H is an enlarged, cross-sectional view of an alternate type of interface between the dose knob and runner of FIGS. 6A and 6B showing detail of an oval rotational interlock.
Figure 6F:
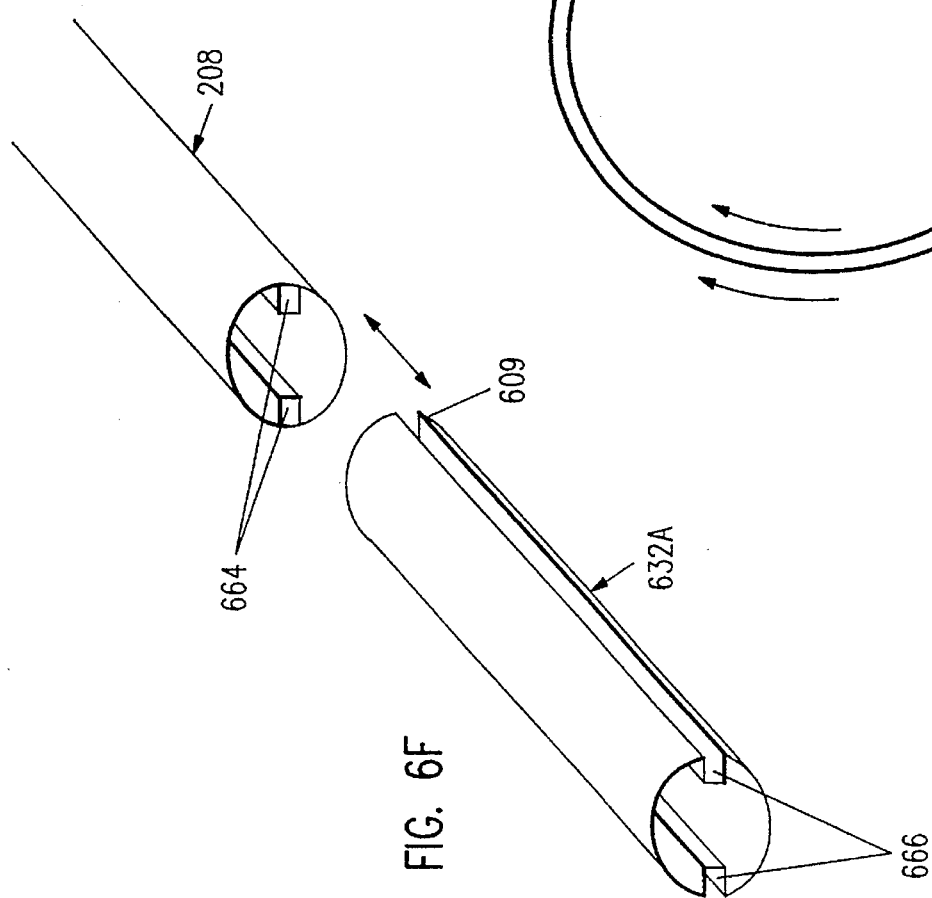
FIG. 6F is an enlarged, perspective view, of a portion of the dose knob and runner of FIGS. 6A and 6B.

FIG. 6G is a cross-sectional view of the rail and groove interlock system of FIG. 6F with runner portion 632A sitting inside dose knob 208. Of course, those skilled in the art will recognize that any number of rails and grooves can be utilized with the same result. Further, it should be noted that the position of the rails 664 and grooves 666 can be reversed. That is to say, the rails can be formed on runner 632 with the grooves formed in dose knob 208. This configuration would yield the same result. The set of grooves and the set of rails are illustrative of a first rotational interlocking structure and a second rotational interlocking structure, respectively, wherein the interaction of the first and second rotational interlocking structures rotationally couples the two parts containing the first and second rotational interlocking structures. Consequently, the embodiments shown herein to lock dose knob 208 and runner 632 in rotational motion are illustrative only of the principles of the invention and are not intended to limit the invention to the particular embodiments illustrated.

FIG. 6H shows yet another method of allowing axial freedom of movement ("telescoping"), while preventing independent rotational motion and ensuring rotational communication between dose knob 208 and runner 632. In FIG. 6H, dose knob 208 and runner 632 are not circular cross section tubes but are ovals. This configuration prevents rotational motion simply by virtue of the irregular shapes employed. Once again, it will be apparent to those skilled in the art that shapes other than ovals can be utilized to achieve this effect. Indeed, any shape other than circular would achieve the desired result.

With dose knob 208 and runner 632 in rotationally connected as shown above, it follows that when dose knob 208 is turned, runner 632 and dose knob 208 rotate in together.

Dose-setting sleeve 630 is positioned inside runner 632 (FIGS. 6A and 6B). A system of rails and grooves that is similar to the system coupling dose knob 208 and runner 632, couples runner 632 and dose-setting sleeve 630. Consequently, when dose knob 208 is rotated, runner 632 responds to the rotation of dose knob 208, as described above, and dose-setting sleeve 630 responds to the rotation of runner 632, yet dose-setting sleeve 630 is free to move axially within runner 632. Thus, dose knob 208, runner 632, and dose-setting sleeve 630 rotate together, but yet can "telescope" up and down axis 202 (FIG. 2) of housing 304.

This "telescoping" action allows dose knob 208 to rotationally communicate with dose-setting sleeve 630 even when the variable dosing assembly 306 is in the "activated" or extended position. Dose-setting sleeve 630 has threads 631 on its interior surface which interact with threads 654 on pushrod 316. This interaction causes dose-setting sleeve 630 to move up and down pushrod 316 when dose-setting sleeve 630 is rotated. When the patient rotates dose knob 208, the position of dose-setting sleeve 630 and rachet sleeve 624 on pushrod 316 is adjusted and a new dose is set. Hence, the interaction between threads 631 on the inner surface of dose-setting sleeve 630 and threads 654 on pushrod 316 allows for precise manual dose-setting, as explained more completely below. Rachet sleeve 624 and dose-setting sleeve 630 are made of plastic or some other suitable, moldable material.

Pushrod locking mechanism 626 (FIGS. 6A and 6B) is oval in shape and has a second groove 623 which accepts lip 621 of runner 632 and thereby translationally couples one end of runner 632 to pushrod locking mechanism 626 and cartridge seat 318. Pushrod locking mechanism 626 is made of plastic or some other suitable material.

Needle thrust locking mechanism 642 locks runner 632, medicament cartridge assembly 305 and variable dosing assembly 306 in the retracted position against the force of main spring 704 (FIG. 7). A detailed description of the "cocking" mechanisms and procedure is provided below.

When medicament injection apparatus 200 is in the retracted position rachet sleeve 624 and thus pushrod 316 are held in place by rachet interlock portion 618 of pushrod locking mechanism 626. The dose can be adjusted by manipulating dose knob 208 which causes rachet sleeve 624 to "rachet" up rachet interlock portion 618 of pushrod locking mechanism 626. Consequently, in the retracted position, rachet sleeve 624, dose-setting sleeve 630, and pushrod 316 are held in relative position ready to administer the proper dose unless a deliberate effort is made by the patient to change the dose, thus, rachet sleeve 624 and pushrod locking mechanism 626 prevent inadvertent dose changes when medicament injection apparatus 200 is in the retracted position or "cocked" and ready for use.

Figure 7A:
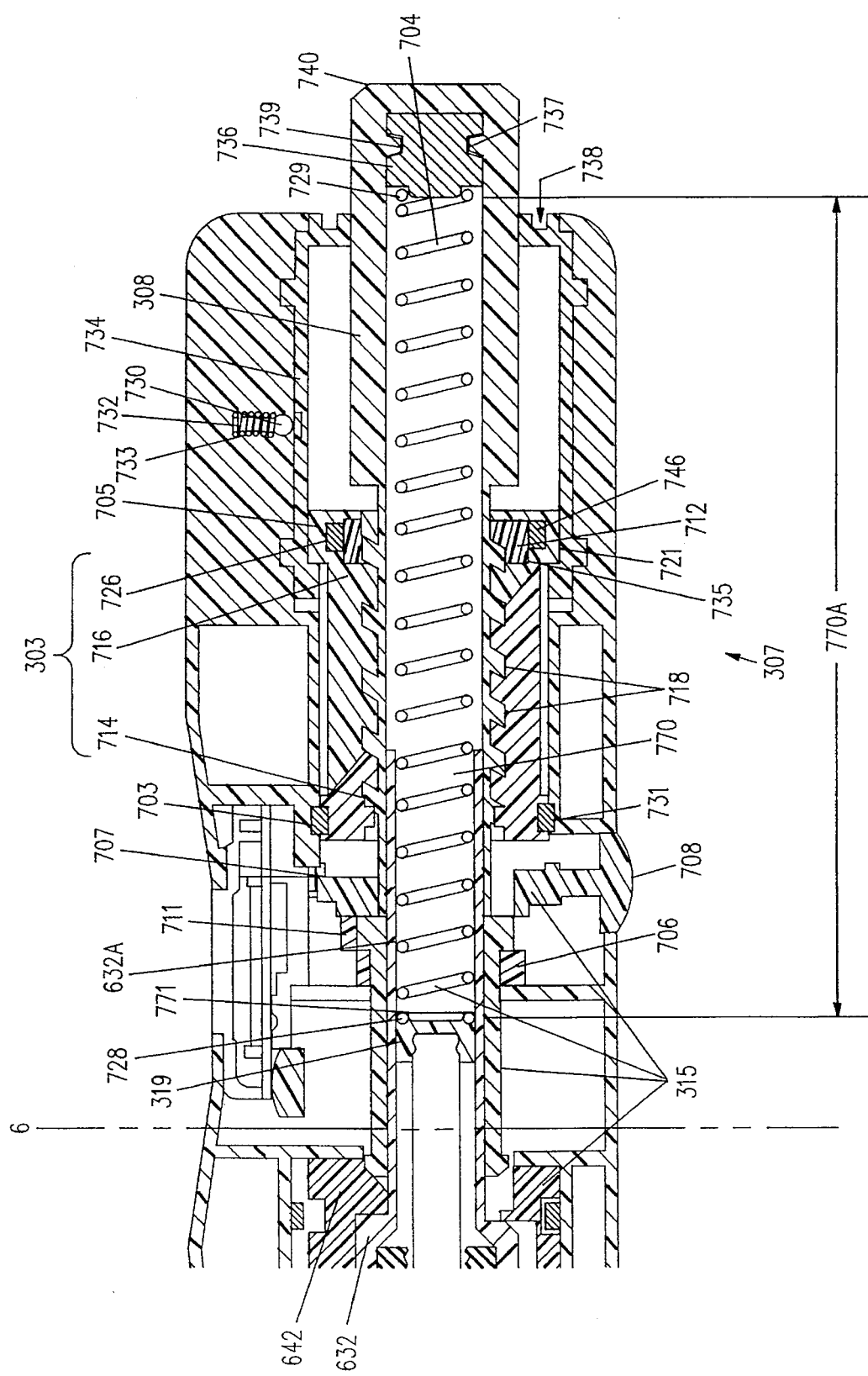
FIG. 7A is an enlarged, fragmentary, front elevation view, in cross section, of a portion of a medicament injection apparatus constructed in accordance with the present invention including the automatic dosing assembly.

As described in more detail below, upon needle thrust activation by the user, e.g., upon depression of dose knob 208 beyond its initial "cocked" position, main spring 704 (FIG. 7A) pushes against thrust bearing 319 and end 660B of pushrod 316 (FIG. 6C) and forces pushrod 316 in forward direction 204 (FIG. 2). As a result, medicament cartridge assembly 305, pushrod subassembly 306A, runner 632 and dosing sleeve subassembly 314, including ratchet sleeve 624, dose-setting sleeve 630 and pushrod locking mechanism 626, are thrust forward by main spring 704 (FIG. 7A). Consequently medicament cartridge assembly 305 is shifted to the "activated" or extended position and needle 201 is thrust in forward direction 204. These components move in unison because,as described above, they are interlocked for axial motion. Thus, they move in forward direction 204 as one unit until tapered edge surface 612 of pushrod locking mechanism 626 engages tapered cam portion 614 of housing 304, which, in turn, causes rachet interlock portion 618 to be released, i.e., moved in a direction so that rachet interlock teeth 620 disengage and release rachet sleeve teeth 629. Once rachet sleeve 624 is released pushrod 316 is free to continue to move forward independently of pushrod locking mechanism 626, cartridge seat 318 and runner 632. As pushrod 316 moves in forward direction 204 along axis 202, pushrod 316 and pushrod piston head 317 force plunger 524 towards end 531 of vial 520A. This action forces medicament 503 out of vial 520A through needle 201 until end 625 of rachet sleeve 624 contacts rachet sleeve stop 627 of cartridge seat 318.

The combination of variable dosing assembly 306 and medicament cartridge assembly 305 allows the patient to ensure proper self-administration of an accurate and adjustable amount of medicament 503 with minimal discomfort or trauma. This is a marked improvement over prior art systems and makes a considerable contribution to the quality of life enjoyed by these patients.

Figure 7B:
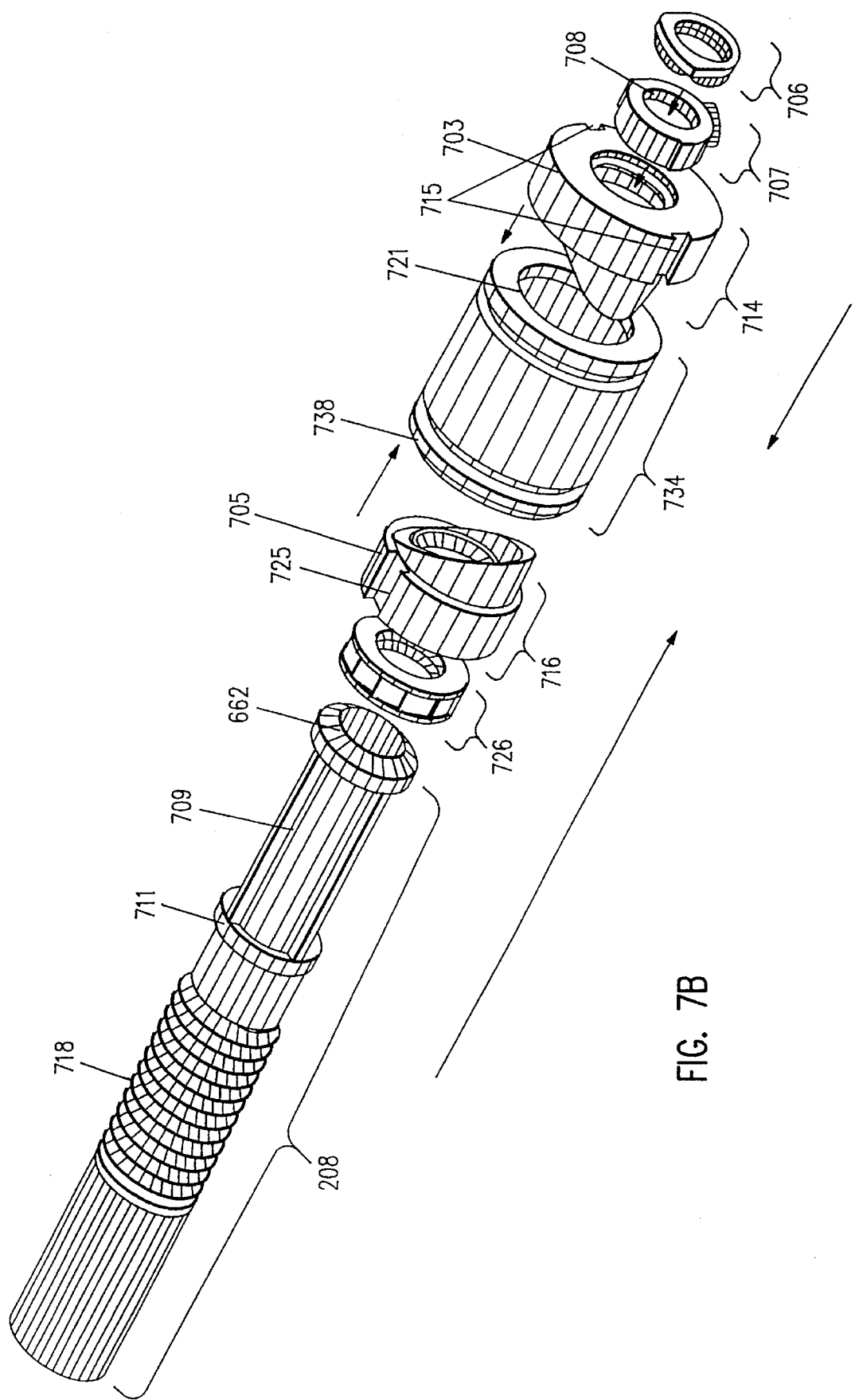
FIG. 7B is an exploded, top perspective view, of the dose knob dose display cam system, lock ring with dose reset button, stationary angled cylinder, dose-limiting sleeve, rotating angled cylinder, and rachet wind down bearing of FIG. 7A.

Space 659 (FIG. 7) is provided within housing 304 for an optional digital or analog dose meter 655. The type of dose meter 655, if any, selected depends on the desired production cost of medicament injection apparatus 200. The dose meter 655 interacts with dose knob 208 via dose knob grooves 709 (FIG. 7B) on dose knob 208 and dosing readout cams 706 (FIG. 7B). These mechanisms are well known in the art and their detailed description is omitted here so as not to detract from the novel features of the present invention.

Automatic Dosing Assembly

FIG. 7A is an enlarged front elevation cross-sectional view of automatic dosing assembly 307. FIG. 7B is an exploded, top perspective view of dose knob 208, dose display cam system 706, lock ring 707 with dose reset button 708, stationary hollow angled cylinder 714, dose-limiting sleeve 734, rotating hollow angled cylinder 716, and rachet wind down bearing 726, each of which are explained more completely below.

Automatic dosing assembly 307 includes a dose knob stop assembly 303 and a thrusting assembly 315 with dose knob 208 and motive force subassembly 300 (FIG. 3). In one embodiment, dose knob stop assembly 303 includes stationary angled cylinder 714, rotating angled cylinder 716 and rachet wind down bearing 726. Thrusting assembly 315 includes dose knob 208, needle thrust locking mechanism 642, lock ring 707 with reset button 708, and motive force subassembly 300. Motive force subassembly 300 includes main spring 704 and thrust bearings 319 and 739 (FIG. 3). Angled cylinders 714 and 716 are, in one embodiment, plastic and are designed to fit together to form a single cylinder in a full interface position as shown in FIG. 7A. When cylinders 714 and 716 are in the full interface position, the maximum automatic dose is administered by medicament injection apparatus 200, as explained below.

Figure 7D:
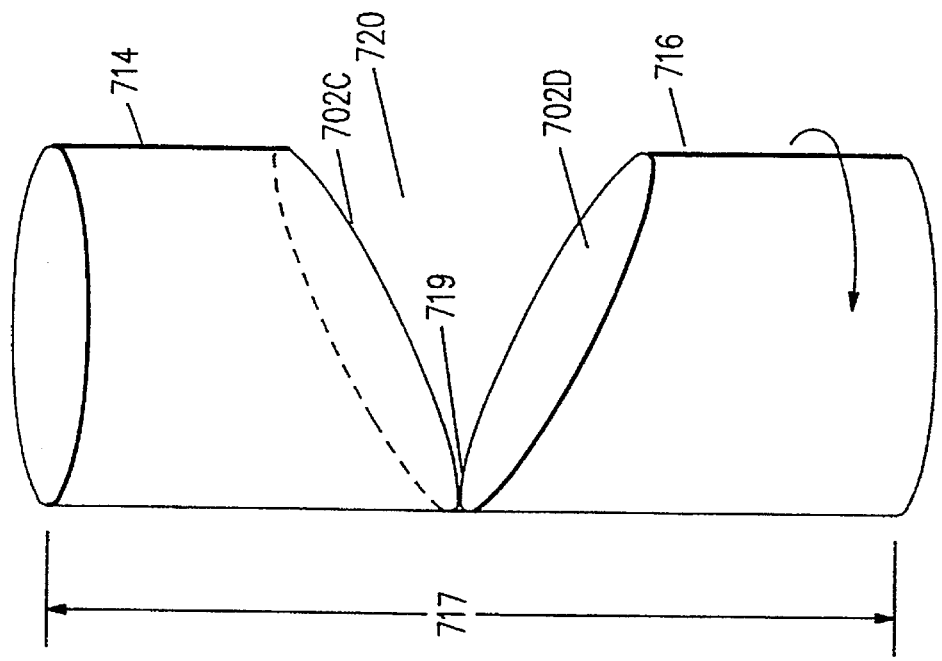
FIG. 7D is a side view of the rotating angled cylinder and stationary angled cylinder of FIGS. 7A and 7B in the partial interface position.
Figure 7C:
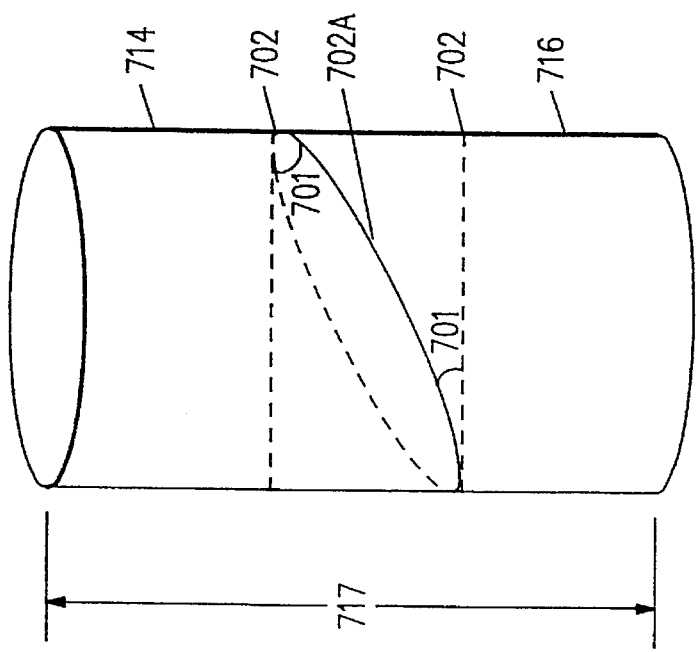
FIG. 7C is a side view of the rotating angled cylinder and stationary angled cylinder of FIGS. 7A and 7B in the full interface position.

FIG. 7C also shows angled cylinders 714 and 716 in this maximum dose, full interface position. As noted above, in the full interface position, angled cylinders 714, 716 form a single continuous cylindrical shape. A gap 720 between cylinders 714, 716 is created by rotating angled cylinder 716 so that surfaces 702C and 702D of angled cylinders 714 and 716, respectively, only partially contact each other. Since surfaces 702C and 702D of cylinders 714 and 716, respectively, can partially contact each other in a continuum of possible partial interface positions, the size of gap 720 is continuously variable. For example, one partial interface position is shown in FIG. 7D where cylinders 714, 716 contact each other only at point 719.

When cylinders 714, 716 are in the full interface position, length 717 has a minimum value. Conversely, when cylinders 714, 716 contact only at point 719, length 717 has a maximum value. Thus, as cylinder 716 is rotated, length 717 varies between the minimum value and the maximum value. The minimum and maximum values of length 717 depends on the dimensions of angled cylinders 714, 716 and the angle 701 between a horizontal line 702 and the interface surface line 702A of angled cylinders, 714, 716, in the full interface position (FIG. 7C). These dimensions including angle 702 are variable and will depend on the requirements of the patient and the manufacturers specific designs for a specific embodiment.

Stationary angled cylinder 714 is mounted on a hollow cylindrical base 703 that has an outside diameter that is greater than the outside diameter of cylinder 714. Cylindrical base 703 has two axial grooves 715 (FIG. 7B) oriented 180° apart, in this embodiment, formed in its outer surface which mate with complementary axial rails 731 on housing 304 (FIG. 7A). This arrangement serves to lock stationary angled cylinder 714 in a fixed rotational position.

Similar to stationary angled cylinder 714, rotating angled cylinder 716 is mounted on a hollow cylindrical base 705 that has an outside diameter that is greater than the outside diameter of cylinder 716. In this embodiment, the outside diameter of cylindrical base 705 is about the same as the inside diameter of dose-limiting sleeve 734 so that cylinder 716 and cylindrical base 705 both fit inside dose-limiting sleeve 734.

Figure 7G:
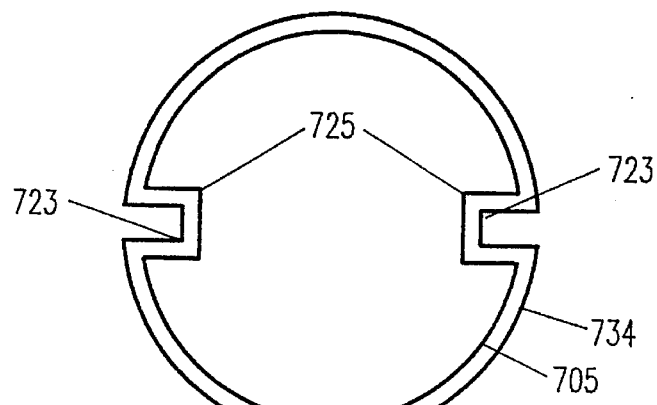
FIG. 7G is an enlarged, cross-sectional view, of the interface of the dose-limiting sleeve and the rotating angled cylinder of FIGS. 7A and 7B showing detail of the rail and groove rotational interlock.

Specifically, rotating angled cylinder 716 is fitted inside dose-limiting sleeve 734 at it's forward end 721 and is rotationally coupled to dose-limiting sleeve 734 by rails 723 (FIG. 7G) on the inside diameter of dose-limiting sleeve 734 that fit into corresponding grooves 725 (FIG. 7G) on the outside diameter of cylindrical base 705. This configuration is shown in FIG. 7G where rails 723 on the interior surface of dose-limiting sleeve 734 interlock with grooves 725 on the exterior surface of rotating angled cylinder base 705. This rail and grove system is similar to that set forth above with respect to dose knob 208 and runner 632.

The rail and groove system causes rotating angled cylinder 716 to rotate when dose-limiting sleeve 734 is rotated, which in turn changes the orientation of rotating angled cylinder 716 with respect to stationary angled cylinder 714 and increases or decreases gap 720. This action controls axial length 717 occupied by dose knob stop assembly 303 (FIGS. 7C and 7D).

Figure 7H:
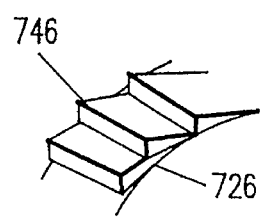
FIG. 7H is an enlarged, angled view of a portion of the rachet wind down bearing of FIGS. 7A and 7B including the rachet teeth.
Figure 7I:
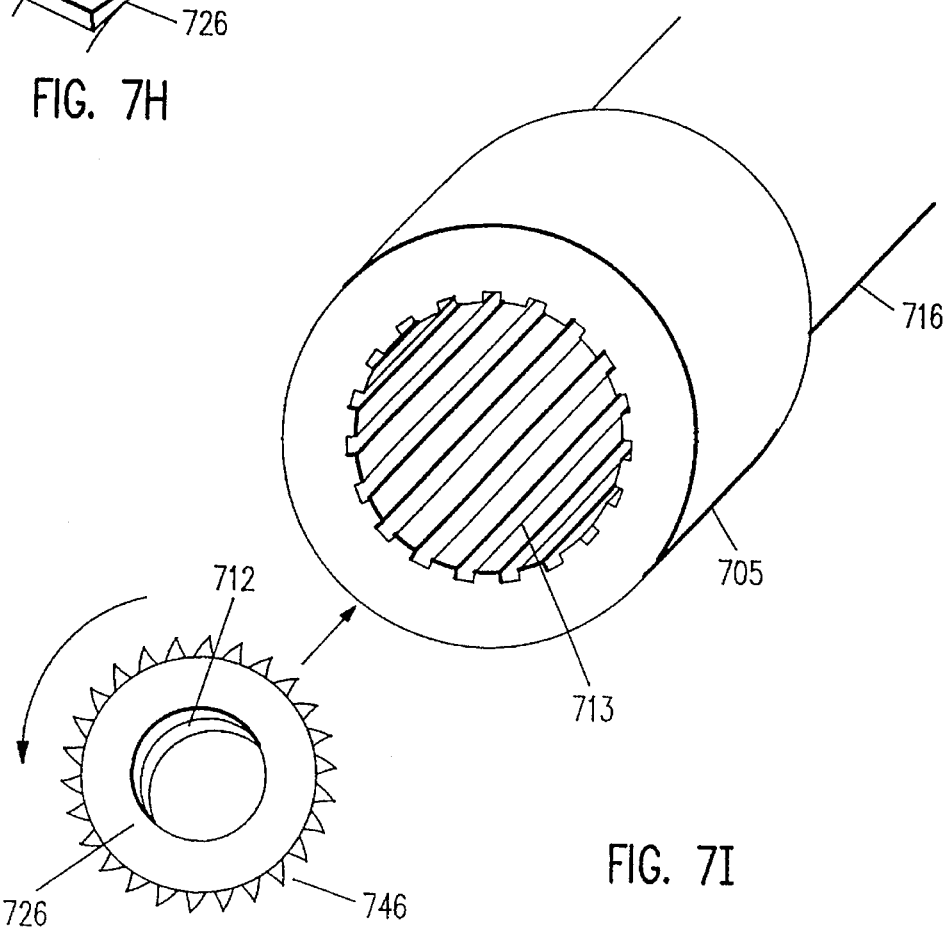
FIG. 7I is an enlarged, angled view of the interior surface of the rotating angled cylinder and the rachet wind down bearing of FIGS. 7A and 7B.

Rachet wind down bearing 726 (FIGS. 7A and 7B) is secured within rotating angled cylinder 716 by radial groove 735 of rotating angled cylinder base 705. Rachet teeth 746 prevent motion of rachet wind down bearing 726 in a first rotational directional, e.g., the clockwise direction, by interacting with complementary axial grooves 713 (FIG. 7G) on the inner surface of rotating angled cylinder base 705. However, rachet wind down bearing 726 is free to rotate in a second rotational direction that is opposite to the first rotational direction, e.g., in the counter-clockwise direction. FIG. 7H shows an enlarged section of the outer surface of rachet wind down bearing 726 and rachet teeth 746. FIG. 7G shows rachet wind down bearing 726 and inner surface 713 of rotating angled cylinder base 705. Since rachet wind down bearing 726 is held within rotating angled cylinder base 705, the two parts, 726 and 716, move translationally along axis 202 (FIG. 3) as one unit.

Rachet wind down bearing 726 is also coupled to dose knob 208 by threads 712 (FIG. 7G) on the interior surface of rachet wind down bearing 726 that mate with threads 718 on dose knob 208, which, in this embodiment, are left-handed coarse threads. Rachet wind down bearing 726 sits between rotating angled cylinder base 705 and threads 718 and so absorbs the rotational motion imposed by threads 718. Thus, rotating angled cylinder 716 does not interact with threads 718. This configuration allows the orientation of rotating angled cylinder 716, with respect to stationary angled cylinder 714, to remain constant even as rotating angled cylinder 716 moves forward and backward along axis 202.

Further, since, in this embodiment, threads 718 are left-handed, when dose knob 208 is rotated in a clockwise direction, rachet wind down bearing 726 rotates in a counter-clockwise direction, threading itself forward, taking rotating angled cylinder 716 with it as a single unit, towards stationary angled cylinder 714.

Once rotating angled cylinder 716 makes contact with stationary angled cylinder 714, rotating angled cylinder 716 and rachet wind down bearing 726 are prevented from moving forward. In this position, rachet wind down bearing 726 locks on dose knob threads 718 and prevents further clockwise rotation of dose knob 208. Dose knob 208 is now in the stop position.

As shown above, with respect to FIGS. 6A and 6B, the actual dose delivered through needle 201 is determined by the number of rotations of dose knob 208. Recall, that dose knob 208 is rotationally coupled to runner 632, which in turn is rotationally coupled to dose-setting sleeve 630. Dose-setting sleeve 630 controls the position of rachet sleeve 624 on pushrod 316, which in turn determines the distance plunger 524 moves and the amount of medicament 503 delivered. Therefore, the orientation of rotating angled cylinder 716 and the size of gap 720 determines a specific, pre-set dose which can be set by simply turning dose knob 208 in a clockwise direction until it stops turning. Of course, those skilled in the art will recognize that by reversing the pitch of threads 718 or the rachet action of rachet wind down bearing 726, the direction of dose knob rotation could be reversed. The fact a clockwise direction of rotation is shown here is merely illustrative and does not limit the invention to this embodiment.

The orientation of rotating angled cylinder 716 with respect to stationary angled cylinder 714 is controlled by rotating dose-limiting sleeve 734. This is because, as described above, rotating angled cylinder base 705 rotationally interlocks with dose-limiting sleeve 734 so that when dose-limiting sleeve 734 is rotated it in turn rotates cylinder 716. When dose-limiting sleeve 734 rotates angled cylinder 716, it increases or decreases gap 720 and length 717. As gap 720 and length 717 change, rotating angled cylinder 716 moves forward and backward within dose-limiting sleeve 734 along axis 202.

Dose-limiting sleeve 734 is rotated by a special wrench or tool that fits inside tool interface 738. This tool can be a wrench or a round key. When the tool is in interface 738 and is then rotated, the tool causes dose-limiting sleeve 734 to rotate as well, which, as shown above, rotates angled cylinder 716. Thus, only a doctor or trained person in possession of this tool can adjust the pre-set maximum dose.

Ball and detent system 730, 732, 733 prevents accidental rotation of dose-limiting sleeve 734. Spring 732 puts pressure on ball 730 which puts pressure on detent 733 in dose-limiting sleeve 734 and prevents it from rotating.

The characteristic described above of using two structures to obtain a variable length is central to the operation of automatic dosing assembly 307. While in this embodiment, angled cylinders are used to generate the variable length, this is only illustrative of the principles of the invention and is not intended to limit the invention to the particular shape described herein.

As another example, the two structures used to obtain a variable length 717A can be stepped angled cylinders 714A, 716A with stepped or notched interface surfaces 722A and 722B such as in FIGS. 7E and 7F. Stepped angled cylinder 714A, like angled cylinder 714, includes a base 703A and grooves 715A for mating with rails 731 on housing 304. Stepped angled cylinder 716A, like angled cylinder 716, also includes a base 705A and grooves 725A for coupling to rails 723 on dose-limiting sleeve 734. Stepped angled cylinders 714A and 716A operate and interact with the other assemblies of medicament injection apparatus 200 in a manner identical to that described above for angled cylinders 714 and 716. However, stepped angled cylinders 714A and 716A have stepped interface surfaces 722A and 722B, respectively, which provide incremental interface positions rather than the continuum of positions available with angled cylinders 714 and 716. FIG. 7F shows stepped angled cylinders 714A and 716A in the full interface position with interface 702A. These stepped interface positions allow for greater accuracy and stability in setting the automatic dose by interlocking stepped angled cylinders 714A and 716A at each interface position and providing a rachet-like interaction. In this configuration, each interface position would correspond to a minimal increment in the dose delivered. For instance, each interlocking step could correspond to a pre-determined fraction of a milliliter. Thus, the dose delivered could to be determined to any accuracy desired by controlling the spacing of the notches or steps on the interface surfaces 722A and 722B.

The stepped angled cylinder configuration described above is only one of many variations possible which achieve the results of the present invention and perform the function of dose knob stop assembly 303. The particular configuration chosen will depend on the requirements of the patient and the manufacturer with respect to cost and dose accuracy desired.

As shown above, automatic dosing assembly 307 allows for a pre-set dose to be administered quickly and easily by simply rotating dose knob 208, clockwise, to the stop position. For patients who administer the same dose regularly, automatic dosing assembly 307 is highly advantageous because it eliminates the need to read a dose meter or set some other complicated dosing mechanism. Further, automatic dosing assembly 307 is ideal for patients who are blind, as is the case with many diabetics, or suffer from some other disability which makes prior art systems impractical. Additionally, automatic dosing assembly 307 could prove life saving in the application of nerve agent antidotes or allergy antidotes, or when the patient is likely to suffer some form of temporary disability. In these cases, time is of the essence and the patient is likely to be agitated and unable to think clearly enough to employ prior art systems.

Further, in those cases where the patient needs to be able to apply doses which vary from injection to injection, or when a new medicament cartridge 520 is being primed, medicament injection apparatus 200 provides a variable dosing capability. Priming is the operation of expelling air bubbles from cartridge 520 prior to a first use of a medicament cartridge 520. Priming operations are well known to those skilled in the art and are standard procedure. For variable dosing operation the doctor or a trained patient can use the procedure discussed above to pre-set the automatic dose and, as shown above, limit the allowable rotations of dose knob 208. This pre-set automatic dose then represents the maximum allowable dose until it is changed with the special tool. However, a full range of doses less than the pre-set automatic dose can be set by monitoring dose meter 655, while rotating dose knob 208, and simply discontinuing the rotation of dose knob 208 when the desired dose is shown. In this manner any dose up to and including the pre-set automatic dose can be set.

Finally, those skilled in the art will recognize that if a maximum permissible dose is not of concern, only the thrusting assembly of the automatic dosing assembly would be utilized. The resulting medicament injection apparatus would provide manually adjustable doses by simply turning the dose knob, for example, three complete revolutions would be one dose and four complete revolutions another dose. This simple dose adjustment combined with the motion provided by the thrusting assembly would allow accurate and reliable injections in a wide variety of situations including low light or use by a blind person. As is discussed more fully below, in one embodiment, the setting of a variable dose must be done when dose knob 208 has been released by lock ring 707 and is in the extended position.

Medicament injection apparatus 200 combines the flexibility of variable dosing with the convenience and safety of an automatic dose capability. Further, when variable dosing is necessary or desired the doctor can at least set the maximum dose that can be administered, thus preventing overdose in the event of patient error in manually setting the dose. This feature makes medicament injection apparatus 200 suitable for a wide range of applications and patients.

Medicament Injection Apparatus Cocking and Manipulation

In this embodiment, medicament injection apparatus 200 must be "double cocked" prior to placing medicament injection apparatus 200 against the user's skin. This means that both ends 208 and 210 (FIG. 2) of medicament injection apparatus 200 have a "cocked" position and an "extended" position. The cocking operations, as explained below, compress main spring 704. Main spring 704 is part of motive force subassembly 300 which also includes thrust bearings 319 and 739. Motive force subassembly 300 supplies the driving force for medicament injection apparatus 200 (FIG. 7A), e.g., energizes medicament injection apparatus 200. Main spring 704 is a standard coil spring made of steel or some other metal.

As described above portion 632A of runner 632 is tubular and hollow. Runner 632 and dose knob 208 are shaped so that runner 632 can freely slide, e.g., "telescope," up and down, inside of dose knob 208 along axis 202. In one embodiment end 740 of dose knob 208 is closed and end 660B of pushrod 316 with thrust bearing 319 is positioned in portion 632A of runner 632. As described above, pushrod locking mechanism 626 holds the relative position of pushrod 316, and thrust bearing 319, constant until tapered edge surface 612 of pushrod locking mechanism 626 engages tapered cam portion 614 of housing 304. This means pushrod end 660B, with bearing 319 attached, effectively closes end 771 of runner portion 632A. Thus, runner portion 632A, with pushrod 316, and dose knob 208 form an enclosed cavity 770 which has a variable length 770A (FIG. 7A). Variable length 770A is smaller when medicament injection apparatus 200 is in a "cocked" or retracted position and larger when medicament injection apparatus 200 is in "activated" or extended position. Main spring 704 of motive force subassembly 300 is positioned within cavity 770.

One end 728 of main spring 704 is positioned inside portion 632A of runner 632 (FIG. 7A) against thrust bearing 319 which is coupled to radial groove 656 (FIG. 6C) of pushrod 316. Another end 729 of main spring 704 is positioned inside dose knob 208 against thrust bearing 736 which is coupled to dose knob end 740 by radial lip 739 that sits in groove 737 of thrust bearing 736. Thrust bearings 319 and 736 freely rotate to prevent main spring 704 from becoming twisted or kinked during operation.

As described above, dose knob 208 and runner 632 are hollow, tubular parts which fit together with runner portion 632A inside dose knob 208. Thus, main spring 704 is fully contained within these parts and when variable length 770A of cavity 770 gets smaller, i.e., medicament injection apparatus 200 is cocked, main spring 704 is compressed and exerts a force in backward direction 206 (FIG. 2) against dose knob end 740, and a force in forward direction 204 against pushrod 316 (FIG. 2).

Figure 7K:
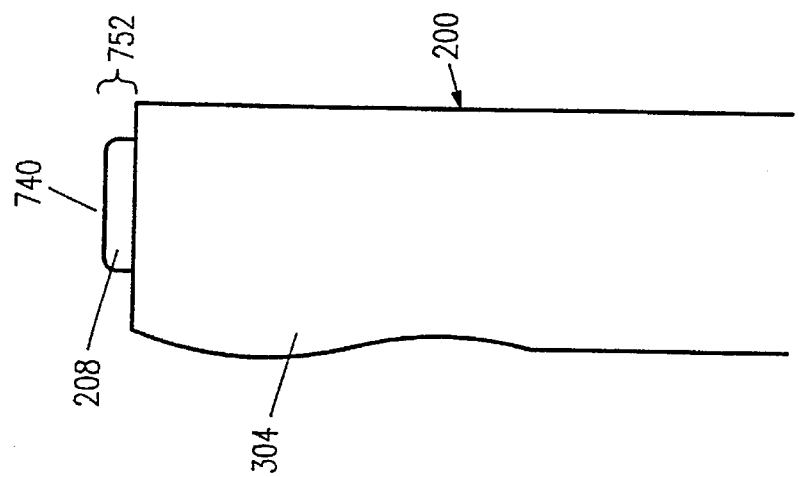
FIG. 7K is an enlarged side view of the dose knob of FIGS. 7A and 7B in the retracted position.
Figure 7J:
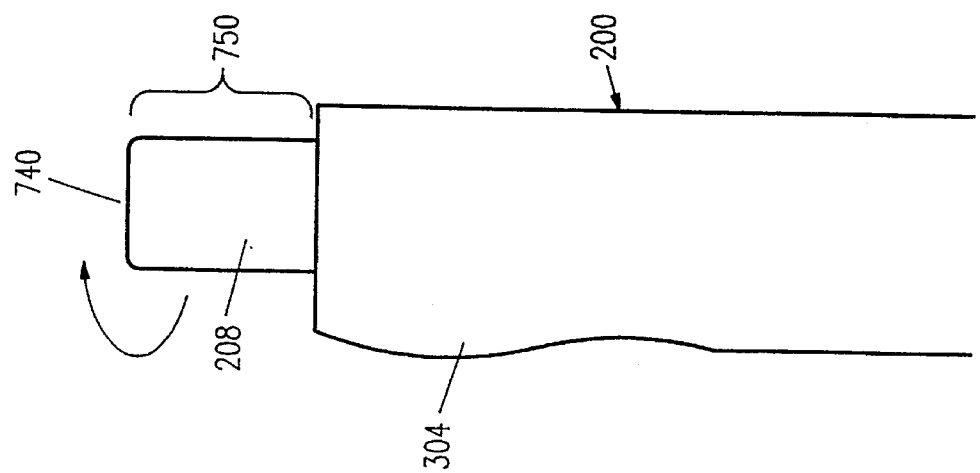
FIG. 7J is an enlarged side view of the dose knob of FIGS. 7A and 7B in the extended position.

Medicament injection apparatus 200 is "cocked" in forward direction 204 to compress main spring 704 so that a force is exerted on dose knob 208 (FIG. 7A) which, on release, thrusts dose knob 208 in backward direction 206, along axis 202 of medicament injection apparatus 200 and leaves dose knob 208 extended outside housing 304. FIG. 7J shows dose knob 208 in the extended position, i.e., prior to forward cocking. FIG. 7K shows dose knob 208 in the retracted position, i.e., after forward cocking. In the extended position dose knob 208 can be accessed easily by the patient to adjust the dose because end 740 is extended distance 750 outside housing 304. However, once medicament injection apparatus 200 is forward cocked, dose knob 208 is no longer accessible to the patient because end 740 only extends distance 752 outside housing 304 which is not sufficient to allow the patient to access and manipulate dose knob 208. Thus, once medicament injection apparatus 200 is cocked in the forward direction the dose is locked.

Cocking in forward direction 204 is accomplished by pushing dose knob end 740 in forward direction 204 towards medicament cartridge assembly 305. This can be accomplished by the patient pressing dose knob end 740 with his or her thumb or pressing close knob end 740 against a flat surface so that dose knob 208 is forced further into housing 304. As dose knob 208 moves into housing 304, radial lip 711 moves past lock ring 707 (FIGS. 7A and 7B). After radial lip 711 passes through lock ring 707, radial lip 711 catches on lock ring 707 and holds dose knob 208 in the "cocked" position. In this position dose knob 208 is situated almost completely within housing 304 and, as described above, dose knob 208 cannot be accessed by the patient to change the dose setting (FIG. 7K).

Cocking in backward direction 206 is accomplished by pushing needle safety cap 302 in backward direction 206, into needle shroud open end 519 (FIG. 5). This can be performed by pressing needle safety cap 302 against a flat surface. As pressure is exerted on the needle safety cap 302, cartridge seat 318 (FIG. 5A), pushrod locking mechanism 626, pushrod 316, and runner 632 are forced towards end 210 of medicament injection apparatus 200. As pushrod 316, along with trust bearing 319, moves towards end 210, main spring 704 is further compressed. The same action moves runner 632 towards end 210 of injector pen 200 and further inside dose knob 208.

Runner 632 includes runner lip 638 which runs radially around the outer circumference of runner 632 (FIG. 6B). Runner lip 638 is shaped so that when it comes into contact with the grooved portion 643 (FIG. 6A) of needle thrust locking mechanism 642, runner 632 is locked into the cocked position (FIGS. 6A and 6B).

Needle thrust locking mechanism 642 is held in contact with runner lip 638 by ring spring 640 which holds needle thrust locking mechanism 642 firmly against runner lip 638 until needle thrust activation.

Once medicament injection apparatus 200 is both forward and backward "cocked," medicament injection apparatus 200 is ready to administer a pre-set dose. This is accomplished by first removing needle safety cap 302 and then placing needle shroud open end 519 firmly against the area to receive the injection. In this position, medicament injection apparatus 200 is ready for "needle thrust activation."

Needle thrust activation occurs by the patient further depressing i.e., pushing forward, dose knob end 740 against main spring 704 and ring spring 640. (The first depression cocked medicament injection apparatus 200 in forward direction 204 and the greater resistance to this second compression indicates to the patient that needle thrust activation is about to occur.) This forward motion further compresses main spring 704 causing beveled lip 662 (FIG. 7B) of dose knob 208 to push forward against tapered cam portion 644 of needle thrust locking mechanism 642 (FIG. 6A). This results in needle thrust locking mechanism 642 being forced outward, in a direction against ring spring 640, so that needle thrust locking mechanism groove 643 disengages runner lip 638.

This action releases runner 632 which through pushrod locking mechanism 626 is coupled to pushrod 316, cartridge seat 318 and medicament cartridge assembly 305. These components are then forced forward by main spring 704 pushing against thrust bearing 319 and end 660B of pushrod 316 (FIG. 7A). Needle 201 of medicament cartridge assembly 305 is thereby forced outside open end 519 of needle shroud 311 and introduced into tissue 210 (FIG. 2). As described above, when tapered edge surface 612 of pushrod locking mechanism 626 engages tapered cam portion 614 of housing 304, pushrod 316 is freed to move in forward direction 204 independently of pushrod locking mechanism 626, runner 632, and cartridge seat 318. Main spring 704 then continues to apply pressure on pushrod 316 which forces medicament 503 through needle 201 as described above. It follows that by depressing end 740 of dosing knob 208, the patient causes both the introduction of needle 201 into tissue 210 and then the administration of an accurate dose of medicament 503.

To administer a second dose, the patient first depresses the dose reset button 708 on lock ring 707. This action forces lock ring 707 outward, releasing lip 711 on dose knob 208, and allowing dose knob 208 to move towards end 210, e.g., backward, under the force of still partially compressed main spring 704. Dose knob 208 is then in the extended position, with end 740 extended beyond housing 304 to allow the patient to manipulate dose knob 208 and change the dose.

When dose knob 208 moves backward under the force of main spring 704, left-handed threads 718 engage rachet wind down bearing 726 and try to rotate it in a clockwise direction. However, as shown above, rachet wind down bearing 726 has rachet teeth 746 on its outer surface which interact with grooves 713 (FIG. 7G) on the inner surface of rotating angled cylinder base 705 and prevent rachet wind down bearing 726 from rotating clockwise. This results in rachet wind down bearing 726 locking in both rotational and axial (i.e. axis 202) position on dose knob 208. Consequently, as dose knob 208 moves towards end 210, rachet wind down bearing 726 and rotating angled cylinder 716 move towards end 210 as well, back into their original position. This action leaves medicament injection apparatus 200 ready to deliver the same automatic dose when the apparatus is double cocked and dose knob 208 is rotated clockwise into its stop position.

As shown above, if a dose other than the pre-set, automatic dose is needed, the patient simply leaves dose knob 208 in the extended position with dose knob end 740 extended distance 750 (FIG. 7J) outside housing 304 and turns dose knob 208 until the desired dose appears on display 655. This procedure is only possible after dose reset button 708 has been depressed and lock ring 707 has released dose knob 208 because, as described above, only in this position is dose knob end 740 extended far enough beyond housing 304 to allow the patient to turn dose knob 208. When injector pen 200 is cocked in backward direction 206, as described above, pushrod locking mechanism 626 re-engages rachet sleeve 624 because pushrod locking mechanism 626 is moved clear of tapered cam 614. At this point the dose can be changed by turning dose knob 208 and causing rachet sleeve 624 to rachet up portion 618 of pushrod locking mechanism 626, however, rachet teeth 629 and 620 prevent accidental changes in the dose by ensuring that any change is resisted and requires a purposeful force. The dose becomes "locked in" once injection pen 200 is cocked in forward direction 204, as described above, and dose knob 208 is once again situated almost completely within housing 304 and therefore inaccessible to the patient. (FIG. 7K)

As shown above, the medicament injection apparatus 200 and method of the present invention is simple to employ. To administer a pre-set dose of medicament the patient need only double cock the apparatus, turn dose knob 208 clockwise to the stop position, remove the needle safety cap 302, place the open end 519 of the needle shroud 311 where the injection is desired and depress dose knob end 740.

By this simple procedure, the needle is automatically injected into the tissue 210 at the proper needle\skin orientation and the proper dose is administered. This is accomplished without the patient ever seeing an exposed needle or having to deal with the psychological or physical problems associated with injecting oneself with an exposed needle. Further, if a dose less than the pre-set automatic dose is desired, the dose can be set manually as shown above.

Medicament injection apparatus 200 of this invention represents considerable improvement over prior art systems and helps provide a better quality of life for patients forced to endure a treatment program of frequent subcutaneous or intramuscular injections.

A detailed description of the operation of one embodiment of the invention is provided above. While this description of the invention is made with reference to a specific embodiment, the description is only illustrative of the invention and is not to be construed as limiting the invention. Various modifications to the present invention can be made to the embodiment described by those skilled in the art without departing from the true spirit and scope of the invention as defined by the appended claims.

I claim:

1. A medicament injection apparatus comprising:
   a housing having:
      an exterior surface, and enclosing an interior volume;
      a first end; and
      a second end opposite said first end;
   a needle shroud removably affixed to said first end of said housing and having an open end removed from said housing;
   a medicament injection assembly, movably mounted in said interior volume of said housing, including:
      an automatic dosing assembly including an automatic dose knob having a stop position,
         wherein upon moving said automatic dose knob to said stop position said automatic dose assembly is set for a predetermined dose; and
         upon engagement and activation of a motive force supplied by said automatic dosing assembly, a plurality of assemblies of said medicament injection assembly move from a first position to a second position in a first direction wherein said first direction is towards said open end of said needle shroud.

2. The medicament injection apparatus of claim 1, wherein one of said plurality of assemblies of said medicament injection assembly comprises:
   a variable dosing assembly movably coupled to said automatic dosing assembly, and having a first end wherein;
      said variable dosing assembly is selectively engaged by said user to dispense a predetermined and adjustable amount of a medicament from said medicament injection apparatus upon engagement and actuation of said medicament injection assembly.

3. The medicament injection apparatus of claim 2, wherein another one of said plurality of assemblies of said medicament injection assembly comprises:
   a medicament cartridge assembly removably affixed to said first end of said variable dosing assembly, and including a first end and a second end opposite said first end wherein said second end is fashioned to accept a medicament cartridge having a first sealed end and a second end opposite said first sealed end which contains a movable plunger.

4. The medicament injection apparatus of claim 3, wherein said medicament cartridge assembly further comprises:

a needle subassembly removably affixed to said first end of said medicament cartridge assembly, and having a needle;
      wherein when said needle subassembly is in said first position, said needle is contained within said needle shroud; and
      when said needle subassembly is in said second position, said needle has an end extending through said open end of said needle shroud.

5. The medicament injection apparatus of claim 4, further comprising:
   a needle safety cap removably affixed to said medicament cartridge assembly wherein said needle safety cap encloses said needle.

6. The medicament injection apparatus of claim 3, wherein said variable dosing assembly further comprises:
   a pushrod subassembly including a pushrod wherein upon engagement and actuation of said automatic dosing assembly, said pushrod engages said plunger and moves said plunger in said first direction inside said medicament cartridge; and
   a dosing sleeve subassembly movably mounted on said pushrod, wherein said dosing sleeve subassembly position on said pushrod determines a distance said pushrod moves in said first direction.

7. The medicament injection apparatus of claim 1, wherein said automatic dosing assembly further comprises:
   a thrusting assembly having a motive force subassembly that is selectively engaged and actuated by a user;
      wherein upon engagement and actuation of said motive force subassembly, said thrusting assembly moves said plurality of assemblies of said medicament injection assembly from said first position to said second position.

8. The medicament injection apparatus of claim 7, wherein said thrusting assembly further comprises:
   a tubular dose knob selectively engagable with a variable dosing assembly of said medicament injection assembly, and having a first open end and a second end opposite to said first open end;
      wherein upon engagement of said tubular dose knob with said variable dosing assembly and movement of said tubular dose knob in a selected direction, said user adjusts an amount of a medicament to be dispensed from said medicament injection apparatus.

9. The medicament injection apparatus of claim 8 wherein said automatic dosing assembly further comprises:
   a dose knob stop subassembly coupled to said tubular dose knob wherein said dose knob stop assembly limits movement of said tubular dose knob in said selected direction and so limits said amount of said medicament to be dispensed from said medicament injection apparatus to a predetermined and pre-set limit.

10. The medicament injection apparatus of claim 9, wherein said dose knob stop assembly further comprises:
    two structures coupled to said tubular dose knob and each of said two structures having a surface wherein said two structures are mounted within said automatic dosing assembly so that said surfaces interact and interface with one another such that a combined length of the two structures is variable depending on a relative position of said two surfaces and further wherein said variable combined length determines said predetermined and pre-set limit.

11. The medicament injection apparatus of claim 10, wherein said dose knob stop subassembly further comprises:

a dose limiting sleeve coupled to at least one of said two structures and selectively engaged by said user to adjust said relative position of said surfaces of said two structures to set said predetermined and pre-set limit.

12. The medicament injection apparatus of claim 11, wherein said dose limiting sleeve comprises a tubular structure having a first end and a second end opposite said first open end wherein one of said two structures is positioned within said first open end of tubular structure.

13. The medicament injection apparatus of claim 12, wherein said one of said two structures includes a set of grooves and said dose limiting sleeve tubular structure includes a set of rails and further wherein said sets of grooves and rails rotationally couple said one of said two structures and said dose limiting sleeve tubular structure so that said one of said two structures and said dose limiting sleeve tubular structure rotate together.

14. The medicament injection apparatus of claim 10, wherein said two structures comprise angled cylinders.

15. The medicament injection apparatus of claim 10, wherein said two structures comprise stepped angled cylinders.

16. The medicament injection apparatus of claim 8 wherein said medicament injection assembly further comprises:

a runner having a first tubular portion and a second tubular portion wherein said first tubular portion has a first open end and a second open end opposite said first open end, and further wherein said second open end of said first tubular portion is coupled to a first open end of said second tubular portion and said second tubular portion has a second open end opposite said first end.

17. The medicament injection apparatus of claim 16, wherein said variable dosing assembly further comprises:

a dosing sleeve subassembly partially positioned within said first open end of said first tubular portion of said runner such that said dosing sleeve subassembly can move back and forth in both said first direction and said second direction within said first tubular portion of said runner;

wherein said second tubular portion of said runner has a smaller cross-section than a cross-section of said first open end of said tubular dose knob so that at least part of said second tubular portion of said runner is positioned inside said first open end of said tubular dose knob and said second tubular portion can move back and forth in both said first direction and said second direction within said tubular dose knob.

18. The medicament injection apparatus of claim 17 wherein said second tubular portion of said runner includes a set of grooves and said tubular dose knob includes a set of rails and further wherein said sets of grooves and rails rotationally couple said runner and said tubular dose knob so that said runner and said tubular dose knob rotate together to move said dosing sleeve subassembly back and forth in both said first direction and said second direction within said first tubular portion of said runner and adjust an amount of medicament dispensed from said medicament injection apparatus.

19. The medicament injection apparatus of claim 18 wherein:

a pushrod of said variable dosing assembly has a first end and a second end opposite said first end wherein said second end of said pushrod is positioned within said first open end of said second tubular portion of said runner; and said second end of said tubular dose knob is closed; and further wherein said second tubular portion of said runner with said pushrod positioned within said first open end of said second tubular portion and said tubular dose knob form an enclosed cavity with a variable length which is smaller when said plurality of assemblies of said medicament injection assembly are in said first position and larger when said plurality of assemblies are in said second position; and said motive force subassembly is positioned inside said cavity such that said motive force subassembly exerts a force on said second end of pushrod in said first direction and said motive force subassembly exerts a force on said tubular dose knob in said second direction when said plurality of assemblies are in said first position.

20. The medicament injection apparatus of claim 19 wherein:

said pushrod and said runner are coupled so that:
when said plurality of assemblies are in said first position said pushrod and said runner are removably affixed; and
when said plurality of assemblies move from said first position to said second position said pushrod and said runner remain removably affixed for a predetermined distance; and
said pushrod is uncoupled from said runner once said pushrod and said runner have moved together said predetermined distance.

21. The medicament injection apparatus of claim 20 wherein said thrusting assembly further comprises:

a lock ring selectively engaging and holding said tubular dose knob against said force exerted in said second direction; and a needle thrust locking mechanism selectively engaging and holding said runner and said pushrod against said force exerted in said first direction.

22. The medicament injection apparatus of claim 21, wherein said motive force subassembly comprises a spring and a thrust bearing.

23. The medicament injection apparatus of claim 1 wherein said medicament injection assembly further comprises:

a thrusting assembly having a motive force subassembly that is selectively engaged and actuated by a user;
wherein upon engagement and actuation of said motive force subassembly, said thrusting assembly moves said plurality of assemblies of said medicament injection assembly from said first position to said second position.

24. The medicament injection apparatus of claim 23, wherein one of said plurality of assemblies of said medicament injection assembly further comprises:

a variable dosing assembly movably coupled to said thrusting assembly, and having a first end wherein;
said variable dosing assembly is selectively engaged by said user to dispense a predetermined and adjustable amount of a medicament from said medicament injection apparatus upon engagement and actuation of said medicament injection assembly.

25. The medicament injection apparatus of claim 24, wherein another one of said plurality of assemblies of said medicament injection assembly further comprises:

a medicament cartridge assembly removably affixed to said first end of said variable dosing assembly, and including a first end and a second end opposite said first end wherein said second end is fashioned to accept a medicament cartridge having a first sealed end and a second end opposite said first sealed end which contains a movable plunger.

26. The medicament injection apparatus of claim 25, wherein said medicament cartridge assembly further comprises:

a needle subassembly removably affixed to said first end of said medicament cartridge assembly, and having a needle;

wherein when said needle subassembly is in said first position, said needle is contained within said needle shroud; and when said needle subassembly is in said second position, said needle has an end extending through said open end of said needle shroud.

27. The medicament injection apparatus of claim 26, further comprising:

a needle safety cap removably affixed to said medicament cartridge assembly wherein said needle safety cap encloses said needle.

28. The medicament injection apparatus of claim 25, wherein said variable dosing assembly further comprises:

a pushrod subassembly including a pushrod wherein upon engagement and actuation of said thrusting assembly, said pushrod engages said plunger and moves said plunger in said first direction inside said medicament cartridge; and a dosing sleeve subassembly movably mounted on said pushrod, wherein said dosing sleeve subassembly position on said pushrod determines a distance said pushrod moves in said first direction.

29. The medicament injection apparatus of claim 25, wherein said thrusting assembly further comprises:

a tubular dose knob selectively engagable with said variable dosing assembly of said medicament injection assembly, and having a first open end and a second end opposite to said first open end;

wherein upon engagement of said tubular dose knob with said variable dosing assembly and movement of said tubular dose knob in a selected direction, said user adjusts an amount of a medicament to be dispensed from said medicament injection apparatus.

30. The medicament injection apparatus of claim 25 wherein said medicament injection assembly further comprises:

a runner having a first tubular portion and a second tubular portion wherein said first tubular portion has a first open end and a second open end opposite said first open end, and further wherein said second open end of said first tubular portion is coupled to a first open end of said second tubular portion and said second tubular portion has a second open end opposite said first end.

31. The medicament injection apparatus of claim 30, wherein said variable dosing assembly further comprises:

a dosing sleeve subassembly partially positioned within said first open end of said first tubular portion of said runner such that said dosing sleeve subassembly can move back and forth in both said first direction and said second direction within said first tubular portion of said runner;

wherein said second tubular portion of said runner has a smaller cross-section than a cross-section of said first open end of said tubular dose knob so that at least part of said second tubular portion of said runner is positioned inside said first open end of said tubular dose knob and said second tubular portion can move back and forth in both said first direction and said second direction within said tubular dose knob.

32. The medicament injection apparatus of claim 31 wherein said second tubular portion of said runner includes a set of grooves and said tubular dose knob includes a set of rails and further wherein said sets of grooves and rails rotationally couple said runner and said tubular dose knob so that said runner and said tubular dose knob rotate together to move said dosing sleeve subassembly back and forth in both said first direction and said second direction within said first tubular portion of said runner and adjust an amount of medicament dispensed from said medicament injection apparatus.

33. The medicament injection apparatus of claim 32 wherein:

said pushrod has a first end and a second end opposite said first end wherein said second end of said pushrod is positioned within said first open end of said second tubular portion of said runner; and said second end of said tubular dose knob is closed; and further wherein said second tubular portion of said runner with said pushrod positioned within said first open end of said second tubular portion and said tubular dose knob form an enclosed cavity with a variable length which is smaller when said plurality of assemblies of said medicament injection assembly are in said first position and larger when said plurality of assemblies are in said second position; and said motive force subassembly is positioned inside said cavity such that said motive force subassembly exerts a force on said second end of pushrod in said first direction and said motive force subassembly exerts a force on said tubular dose knob in said second direction when said plurality of assemblies are in said first position.

34. The medicament injection apparatus of claim 33 wherein:

said pushrod and said runner are coupled so that:

when said plurality of assemblies are in said first position said pushrod and said runner are removably affixed; and when said plurality of assemblies move from said first position to said second position said pushrod and said runner remain removably affixed for a predetermined distance; and said pushrod is uncoupled from said runner once said pushrod and said runner have moved together said predetermined distance.

35. The medicament injection apparatus of claim 34 wherein said thrusting assembly further comprises:

a lock ring selectively engaging and holding said tubular dose knob against said force exerted in said second direction; and a needle thrust locking mechanism selectively engaging and holding said runner and said pushrod against said force exerted in said first direction.

36. The medicament injection apparatus of claim 35 wherein said motive force subassembly comprises a spring and a thrust bearing.

37. The medicament injection apparatus as in claim 1 wherein, said needle shroud is removably affixed to said first end of said housing by a friction fit.

38. A medicament injection apparatus as in claim 37 wherein, said open end of said needle shroud is removed a first distance from said first end of said housing.

39. The medicament injection apparatus as in claim 38 further comprising:

another needle shroud, wherein upon removal of said needle shroud and removably affixing said another needle shroud to said first end of said housing, an open end of said another needle shroud is removed a second distance, different from said first distance, from said first end of said housing.

40. A medicament injection apparatus as in claim 37 further comprising:

at least two needle shrouds in addition to said needle shroud;
wherein each of said at least two needle shrouds can be individually removably affixed to said first end of said housing;
upon individually removably affixing said at least two needle shrouds to said first end of said housing, each of said at least two needle shrouds have an open end removed a predetermined distance from said first end of said housing; and
said predetermined distance is different for each of said at least two needle shrouds.

41. A medicament injection apparatus comprising:

a housing having:
an exterior surface and enclosing an interior volume;
a first end; and
a second end opposite said first end;
a needle shroud removably affixed to said first end of said housing and having an open end removed from said housing;
a medicament cartridge assembly movably mounted, in said interior volume of said housing so that upon application of a motive force, said medicament cartridge assembly moves from a first position to a second position in a first direction wherein said first direction is towards said open end of said needle shroud, and further wherein said medicant cartridge includes:
a first end;
a second end opposite said first end wherein said second end is fashioned to accept a medicament cartridge having a first sealed end and a second end opposite said first sealed end which contains a movable plunger and;
a variable dosing assembly having a first end removably affixed to said second end of said medicament cartridge assembly and a second end wherein;
said variable dosing assembly is selectively engaged by said user to control a predetermined and adjustable amount of medicament expelled from said medicament cartridge following application of said motive force; and
an automatic dosing assembly removably affixed to said second end of said variable dosing assembly and mounted in said interior volume of said housing, said automatic dosing assembly including an automatic dose knob having a stop position;
wherein upon moving said automatic dose knob to said stop position said automatic dose assembly is set for a predetermined dose; and
upon engagement and actuation of said automatic dosing assembly, said automatic dosing assembly supplies said motive force to said variable dosing assembly and said medicament cartridge assembly thereby moving said variable dosing assembly and said medicament cartridge assembly from said first position to said second position.

42. The medicament injection apparatus of claim 41, further comprising:

a needle subassembly removably affixed to said first end of said medicament cartridge assembly, and having a needle;
wherein when said medicament cartridge assembly is in said first position, said needle is contained within said needle shroud; and
when said medicament cartridge assembly is in said second position said needle has an end extending through said open end of said needle shroud.

43. The medicament injection apparatus of claim 42, further comprising:

a needle safety cap removably affixed to said medicament cartridge assembly wherein said needle safety cap encloses said needle.

44. The medicament injection apparatus of claim 41, wherein said variable dosing assembly further comprises:

a pushrod subassembly including a pushrod wherein upon engagement and actuation of said automatic dosing assembly, said pushrod engages said plunger and moves said plunger in said first direction inside said medicament cartridge; and
a dosing sleeve subassembly movably mounted on said pushrod, wherein said dosing sleeve subassembly position on said pushrod determines a distance said pushrod moves in said first direction.

45. The medicament injection apparatus of claim 41, wherein said automatic dosing assembly further comprises:

a thrusting assembly having a motive force subassembly that is selectively engaged and actuated by a user;
wherein upon engagement and actuation of said motive force subassembly, said thrusting assembly moves said variable dosing assembly and said medicament cartridge assembly from said first position to said second position.

46. The medicament injection apparatus of claim 45, wherein said thrusting assembly further comprises:

a tubular dose knob selectively engagable with said variable dosing assembly and having a first open end and a second end opposite to said first open end;
wherein upon engagement of said tubular dose knob with said variable dosing assembly and movement of said tubular dose knob in a selected direction, said user adjusts an amount of a medicament to be dispensed from said medicament injection apparatus.

47. The medicament injection apparatus of claim 46, wherein said automatic dosing assembly further comprises:

a dose knob stop subassembly coupled to said tubular dose knob wherein said dose knob stop assembly limits movement of said tubular dose knob in said selected direction and so limits said amount of said medicament to be dispensed from said medicament injection apparatus to a predetermined and pre-set limit.

48. The medicament injection apparatus of claim 47, wherein said dose knob stop assembly further comprises:

two structures coupled to said tubular dose knob and each of said two structures having a surface wherein said two structures are mounted within said automatic dosing assembly so that said surfaces interact and interface with one another such that a combined length of the two structures is variable depending on a relative position of said two surfaces and further wherein said variable combined length determines said predetermined and pre-set limit.

49. The medicament injection apparatus of claim 48, wherein said dose knob stop subassembly further comprises:
a dose limiting sleeve coupled to at least one of said two structures and selectively engaged by said user to adjust said relative position of said surfaces of said two structures to set said predetermined and pre-set limit.

50. The medicament injection apparatus of claim 49, wherein said dose limiting sleeve comprises a tubular structure having a first open end and a second end opposite said first open end wherein one of said two structures is positioned within said first open end of tubular structure.

51. The medicament injection apparatus of claim 50, wherein said one of said two structures includes a set of grooves and said dose limiting sleeve tubular structure includes a set of rails and further wherein sets of grooves and rails rotationally couple said one of said two structures and said dose limiting sleeve tubular structure so that said one of said two structures and said dose limiting sleeve tubular structure rotate together.

52. The medicament injection apparatus of claim 51, wherein said two structures comprise angled cylinders.

53. The medicament injection apparatus of claim 51, wherein said two structures comprise stepped angled cylinders.

54. The medicament injection apparatus of claim 51, wherein said medicament injection apparatus further comprises:
a runner having a first tubular portion and a second tubular portion wherein said first tubular portion has a first open end and a second open end opposite said first open end, and further wherein said second open end of said first tubular portion is coupled to a first open end of said second tubular portion and said second tubular portion has a second open end opposite said first end.

55. The medicament injection apparatus of claim 54, wherein said variable dosing assembly further comprises:
a dosing sleeve subassembly partially positioned within said first open end of said first tubular portion of said runner such that said dosing sleeve subassembly can move back and forth in both said first direction and said second direction within said first tubular portion of said runner;
wherein said second tubular portion of said runner has a smaller cross-section than a cross-section of said first open end of said tubular dose knob so that at least part of said second tubular portion of said runner is positioned inside said first open end of said tubular dose knob and said second tubular portion can move back and forth in both said first direction and said second direction within said tubular dose knob.

56. The medicament injection apparatus of claim 55, wherein said second tubular portion of said runner includes a set of grooves and said tubular dose knob includes a set of rails and further wherein said sets of grooves and rails rotationally couple said runner and said tubular dose knob so that said runner and said tubular dose knob rotate together to move said dosing sleeve subassembly back and forth in both said first direction and said second direction within said first tubular portion of said runner and adjust an amount of medicament dispensed from said medicament injection apparatus.

57. The medicament injection apparatus of claim 56, wherein:
said pushrod has a first end and a second end opposite said first end wherein said second end of said pushrod is positioned within said first open end of said second tubular portion of said runner; and
said second end of said tubular dose knob is closed; and further wherein
said second tubular portion of said runner with said pushrod positioned within said first open end of said second tubular portion and said tubular dose knob form an enclosed cavity with a variable length which is smaller when said variable dosing assembly and said medicament cartridge assembly are in said first position and larger when said variable dosing assembly and said medicament cartridge assembly are in said second position; and
said motive force subassembly is positioned inside said cavity such that said motive force subassembly exerts a force on said second end of pushrod in said first direction and said motive force subassembly exerts a force on said tubular dose knob in said second direction when said variable dosing assembly and said medicament cartridge assembly are in said first position.

58. The medicament injection apparatus of claim 57 wherein:
said pushrod and said runner are coupled so that:
when said variable dosing assembly and said medicament cartridge assembly are in said first position said pushrod and said runner are removably affixed; and
when said variable dosing assembly and said medicament cartridge assembly move from said first position to said second position said pushrod and said runner remain removably affixed for a predetermined distance; and
said pushrod is uncoupled from said runner once said pushrod and said runner have moved together said predetermined distance.

59. The medicament injection apparatus of claim 58, wherein said thrusting assembly further comprises:
a lock ring selectively engaging and holding said tubular dose knob against said force exerted in said second direction; and
a needle thrust locking mechanism selectively engaging and holding said runner and said pushrod against said force exerted in said first direction.

60. The medicament injection apparatus of claim 59, wherein said motive force subassembly comprises a spring and a thrust bearing.

61. A medicament injection apparatus as in claim 45 wherein,
said open end of said needle shroud is removed a first distance from said first end of housing.

62. The medicament injection apparatus as in claim 61 further comprising:
another needle shroud, wherein upon removal of said needle shroud and removably affixing said another needle shroud to said first end of said housing, said open end of said another needle shroud is removed a second distance, different from said first distance, from said first end of said housing.

* * * * *